US006203799B1

(12) United States Patent
Mekalanos et al.

(10) Patent No.: US 6,203,799 B1
(45) **Date of Patent: *Mar. 20, 2001**

(54) *VIBRIO CHOLERAE* MUTANTS WHICH ARE SOFT-AGAR PENETRATION DEFECTIVE AND LACK A FUNCTIONAL CTXA SUBUNIT

(75) Inventors: John J. Mekalanos, Cambridge; Claudette L. Gardel, Brighton; Andrew Camilli, Chestnut Hill, all of MA (US)

(73) Assignee: Presidents and Fellows of Harvard College, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/349,403

(22) Filed: Dec. 2, 1994

Related U.S. Application Data

(63) Continuation-in-part of application No. 08/178,055, filed on Jan. 6, 1994, now abandoned, and a continuation-in-part of application No. PCT/US93/06270, filed on Jul. 1, 1993.

(51) Int. Cl.[7] ........................ A61K 39/02; A61K 39/106; C12N 1/00; C12N 15/09

(52) U.S. Cl. ..................................... 424/235.1; 424/261.1; 424/200.1; 424/184.1; 424/203.1; 424/252.1; 435/69.3; 435/909; 435/243; 435/252.3

(58) Field of Search ............................. 424/235.1, 261.1, 424/200.1, 203.1, 184.1, 252.1; 435/693, 909, 243, 252.3

(56) References Cited

U.S. PATENT DOCUMENTS

| | | | |
|---|---|---|---|
| 4,882,278 | 11/1989 | Mekalanos | 435/172.3 |
| 4,935,364 | 6/1990 | Kaper et al. | 435/172.3 |
| 5,098,998 | 3/1992 | Mekalanos et al. | 530/350 |
| 5,135,862 * | 8/1992 | Kaper et al. . | |
| 5,399,494 * | 3/1995 | Kaper et al. . | |
| 5,874,088 * | 2/1999 | Mekalanos | 424/200.1 |

FOREIGN PATENT DOCUMENTS

| | | |
|---|---|---|
| WO 91/18979 | 12/1991 | (WO) . |
| WO 94 01533 | 1/1994 | (WO) . |

OTHER PUBLICATIONS

Gumbiner, Am. J. Physiol. 253 (Cell Physiol. 22):C749–C758, 1987.*

Lima, Curr. Opin. Infect. Dis., 7:592–601, 1994.*

Taylor et al, J. Infect. Dis. 170:1518–1523, 1994.*

Kaper et al., In: *Vibrio Cholerae* and Cholera: Molecular to Global Perspectives Editor Wachsmuth et al pp. 145–176, 1994.*

Tacket et al Infect. & Imm. 66/2:692–695, 1998.*

Ichinese et al, Infect & Imm. 55/5:1090–1093, 1987.*

Trucksis et al, PNAS., 90:5267–5271, 1993.*

Migasewa et al., Infection and Immunity 57: 117–20 (1989).

Cash et al., "Response of Man to Infection with *Vibrio cholerae,* II, Protection from Illness Afforded by Previous Disease and Vaccine", Journal of Infectious Diseases 130:325–333, 1974.

Finkelstein, "Cholera", Critical Reviews in Microbiology 2:553–623, 1973.

Freter et al., "Adhesive Properties of *Vibrio cholerae:* Nature of the Interaction With Intact Mucosal Surfaces" Infection and Immunity 14:246–256, 1976.

Freter et al., "Role of Chemotaxis in the Association of Motile Bacteria With Intestinal Mucosa: Fitness and Virulence of Nonchemotactic *Vibrio cholerae* Mutants in Infant Mice" Infection and Immunity 34:222–233, 1981.

Freter et al., "Role of Chemotaxis in the Association of Motile Bacteria with Intestinal Mucosa: In Vivo Studies" Infection and Immunity 34:234–240, 1981.

Guentzel et al., "Motility as a Virulence Factor for *Vibrio cholerae*" Infection and Immunity 11:890–897, 1975.

Herrington et al., "Toxin, Toxin–coregulated Pili, and the toxR Regulon are Essential for *Vibrio Cholerae* Pathogenesis in Humans", J. Experimental Medicine 168:1487–1492, 1988.

Jones et al., "Adhesive Properties of Vibrio cholerae: Adhesion to Isolated Rabbit Brush Border Membranes and Hemmagglutinating Activity" Infection and Immunity 14:232–239, 1976.

Jones et al., "Adhesive Properties of *Vibrio cholerae:* Nature of the Interaction With Isolated Rabbit Brush Border Membranes and Human Erythrocytes", Infection and Immunity 14:240–245, 1976.

Kaper et al., "A Recombinant Live Oral Cholera Vaccine", Biotechnology, Apr. 1984, pp. 345–349.

Kaper et al., "Recombinant nontoxinogenic *Vibrio cholerae* strains as attenuated cholera vaccine candidates" Nature 308:655–658, 1984.

Levine et al., "Duration of Infection–Derived Immunity to Cholera", J. Infectious Diseases 143:818–820, 1981.

Levine et al., "The Pathogenicity of Nonenterotoxigenic *Vibrio cholerae* Serogroup 01 Biotype El Tor Isolated from Sewage Water in Brazil", J. Infectious Diseases 145:296–299, 1982.

Levine et al., "Volunteer Studies of Deletion Mutants of *Vibrio cholerae* 01 Prepared by Recombinant Techniques" Infection and Immunity 56:161–167, 1988.

Levine et al., "Safety, immunogenicity, and efficacy of recombinant live oral cholera vaccines, CVD 102 and CVD 103–HgR", The Lancet II:467–470, 1988.

(List continued on next page.)

*Primary Examiner*—Nita Minnifield
(74) *Attorney, Agent, or Firm*—Clark & Elbing LLP; Kristina Bieker-Brady

(57) ABSTRACT

*V. cholerae* vaccine strains which have a soft agar penetration-defective phenotype and methods for making such strains are described. Also described are methods for identifying new genes involved in *V. cholerae* motility and the cloning, identification, and sequencing of *V. cholerae* motB and fliC genes.

26 Claims, 5 Drawing Sheets

OTHER PUBLICATIONS

Mekalanos, "Duplication and Amplification of Toxin Genes in *Vibrio cholerae*", Cell 35:253–263, 1983.

Mekalanos et al., "Cholera toxin genes: nucleotide sequence, deletion analysis and vaccine development", Nature 306:551–557, 1983.

Mekalanos et al., "Isolation of enterotoxin structural gene deletion mutations in *Vibrio cholerae* induced by two mutagenic vibriophages" PNAS USA 79:151–155, 1982.

Mostow et al., "High–Frequency Spontaneous Mutation of Classical *Vibrio cholerae* to a Nonmotile Phenotype", Infection and Immunity 58:3633–3639, 1990.

Pearson et al., "New Attenuated Derivatives of *Vibrio cholerae*", Res. Microbiol. 141:893–899, 1990.

Pierce et al., "Determinants of the Immunogenicity of Live Virulen and Mutant *Vibrio cholerae* 01 in Rabbit Intestine", Infection and Immunity 55:477–481, 1987.

Richardson, "Roles of motility and flagellar structure in pathogenicity of *Vibrio cholerae:* Analysis of motility mutants in three animal models", Infection and Immunity 59:2727–2736, 1991.

Richardson et al., Transposon–induced non–motile mutants of *Vibrio cholerae,* J. General Microbiology 136:717–725, 1990.

Taylor et al., "Use of phoA gene fusions to identify a pilus colonization factor coordinately regulated with cholera toxin", PNAS USA 84:2833–2937, 1987.

Taylor et al., "Safe, live *Vibrio cholerae* vaccines?" Vaccine 6:151–154, 1988.

Teppema et al., "In vivo Adherence and Colonization of *Vibrio cholerae* Strains That Differ in Hemagglutinating Activity and Motility", Infection and Immunity 55:2093–2102, 1987.

van de Walle et al., "Production of cholera toxin subunit B by a mutant strain of *Vibrio cholerae*", Applied Microbiology Biotechnology 33:389–394, 1990.

Wachsmuth et al., "Difference between toxigenic *Vibrio cholerae* 01 from South America and US gulf coast", The Lancet 337:1097–1098, 1991.

Yamamoto et al., "*Vibrio cholerae* 01 Adherance to Villi and Lymphoid Follicle Epithelium: In Vitro Model Using Formalin–Treated Human Small Intestine & Correlation between Adherence & Cell–Associated Hemagglutinin Levels", Infection and Immunity 56:3241–3250, 1988.

Yancey et al.,"Role of Motility in Experimental Cholera in Adult Rabbits", Infection and Immunity 22:387–392, 1978.

Gregory D. Pearson et al. CTX Genetic Element Encodes a Site–Specific Recombination System and an Intestinal Colonization Factor, Proc. Natl. Acad. Sci. USA, vol. 90, 3750–3754, 1993.

Kathleen Richardson et al. "Transposon–Induced non–motile mutants of *Vibrio Cholerae*" Journal of General Microbiology, vol. 136, 717–725, 1990.

Bhattacharjee et al., Bulletin of the World Health Organization 57:123–128, 1979, Adherence of Wild–Type and Mutant Strains of *Vibrio Cholerae* to Normal and Immune Intestinal Tissue.

Blair et al., Journal of Bacteriology 173:4049–4055, 1991, Mutant MOTB Proteins in *Escherichia coli.*

Chun et al., Science 239:279–277, 1988,Bacterial Motility: Membrane Topology of the *Escherichia coli* MOTB Protein.

Hughes et al., Gene 146:79–82, 1994, Sequence Analysis of the *Vibrio Cholerae* ACFD Gene Reveals the Presence of an Overlapping Reading Frame . . . Products of Salmonella.

McCarter et al., Journal of Bacteriology 175:3361–3371, 1993, Identification of Genes Encoding Components of the Swarmer Cell Flagellar Motor and Propeller and a Sigma Factor . . . *Vibrio Parahaemolyticus.*

Wei et al., Journal of Molecular Biology 186:791–803, 1985, Covalent Structure of Three Phase–1 Flagellar Filament Proteins of Salmonella.

* cited by examiner

```
  1  CCCNNNTGGG NCNTNCANNG GCAGNCAGAT CCTGGAAAAC GGGAAAGGTT
 51  CCGTTCAGGA CGCTACTTGT GTATAAGAGT CAGGTCTAGA GAGATTGAGC
101  AAGGAGCCAT TGAAGTGGAA AACTTGGGGN AGCAGATTGA CATTCGGATC
151  CNCGAAAAAG GCGCGTTCCC AGAAGGTTCC GCATTCTTAC AACCTAAGTT
201  CCGCCCTCTG GTACGCCAAA TTGCTGAGTT GGTCAANGAC ATTCCCGGTA
251  AAGTGCGGGT GACAGGGAAC ACTGATAACC AGAAATTGGA CTCTGAACTG
301  TATCGCTCGA GCAAGAGAAC GGAGTGAACC CACCATCCNC GGGATTTATC
351  CTGAATAGAG GCCAGCTTGG CAAGCTCTTC GGCGACCTNG TGGGGGATAA
401  CNCAAAGAGG TGGGGGTCNC AATGGCCAAN AAGTCCGGNA AATTCNTAAA
451  CCCANCTTGG ATTTTTGGGA TTGGGNCCAA CCTTCTTTNC CCCCCGAAAA
501  AACNTGGGTT TGGGGTTNTC GGNAAGCCNC CCNATT  (SEQ ID NO: 3)
```

```
E.coli motB      161       FRTGSADVEPYMRDILRAIAPVLNGIPNRISLSGHTDD        198 (SEQ ID NO: 4)
                           |   ||| ++|   | ++|  || ++   || ++ ++|+||+
Vibrio Query     148 IXEKGAFPEGSAFLQPKFRPLVRQIAELVXDIPGKVRVTGNTDNQKLDSELYRSS 312 (SEQ ID NO: 5)
                     + |   |  | | +     |++||| |+  ||  ++| |+||++ + +  | |+
B.subt. mot hom. 124 LQEAVLFDTGEAKVLKNAETLLHQIAVLLQTIPNDIQVEGHTDSRNISTYRYPSN 178 (SEQ ID NO: 6)
```

Fig. 4

```
DNA sequence   343 b.p.   AGCTCGCTTTAT ... TATCTTCAGGCT   linear

1/1                                     31/11
AGC TCG CTT TAT CGT CCG TGG TAG AAA AAC CTT GAG TGC CAA AGT GCA CTT CCC GTG CAT
S   S   L   Y   R   P   W   *   K   N   L   E   C   Q   S   A   L   P   V   H
61/21                                   91/31
TTT ATG TGT TTG ATG CCT AAT TTA TCG CCA ACC AAA CTT TTT TCT TAA AAA AAT CGA AAA
F   M   C   L   M   P   N   L   S   P   T   K   L   F   S   *   K   N   R   K
121/41                                  151/51
TTT TTC CTA AAG GAT TTA AAA AAC GCG CCG TTA TAA AAG GTA ACT TTG AGA GAA CTA CTT
181/61                                  211/71
TGG TTT TCC GAG ACG TCG GAA ACC GGA TCA ATC GGA AAA TCA ATT GGA GAA ATC ACC|ATG
W   F   S   E   T   S   E   T   G   Y   I   G   K   S   I   G   E   I   T   M
241/81                                  271/91
GCA GTG AAT GTA AAT ACC AAC GTC GCA GCA ATG ACA GCT CAA CGT CAT TTG ACT GGT GCA
A   V   N   V   N   T   N   V   A   A   M   T   A   Q   R   H   L   T   G   A
301/101                                 331/111
ACC AAT GCA CAC CAA ACT CCA CTG GAG CGT CTA TCT TCA GGC T    (SEQ ID NO: 7)
T   N   A   H   Q   T   P   L   E   R   L   S   S   G
```

Fig. 5

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
(A) LENGTH: 20
(B) TYPE: nucleic acid
(C) STRANDEDNESS: single
(D) TOPOLOGY: linear (xi) SEQUENCE DESCRIPTION: SEQ ID NO: 1:

```
CCATCTCATC AGAGGGTAGT                                              20
```

(2) INFORMATION FOR SEQ ID NO: 2:

(i) SEQUENCE CHARACTERISTICS:
(A) LENGTH: 20
(B) TYPE: nucleic acid
(C) STRANDEDNESS: single
(D) TOPOLOGY: linear (xi) SEQUENCE DESCRIPTION: SEQ ID NO: 2:

```
ACCATGTTAG GAGGTCACAT                                              20
```

(2) INFORMATION FOR SEQ ID NO: 3:

(i) SEQUENCE CHARACTERISTICS:
(A) LENGTH: 536
(B) TYPE: nucleic acid
(C) STRANDEDNESS: single
(D) TOPOLOGY: linear (ix) FEATURE:
(D) OTHER INFORMATION: N in positions 4, 5, 6, 11, 13, 15, 18, 19, 25, 130, 152, 237, 339, 389, 402, 418, 430, 439, 446, 455, 476, 486, 502, 517, 522, 528, 532 may be A, T, G, or C. Xaa in position 23 (152) may be Pro, Thr or Ala. Xaa in position 51 (236) may be Met, Thr, Lys or Arg.

(xi) SEQUENCE DESCRIPTION: SEQ ID NO: 3:

```
CCCNNNTGGG NCNTNCANNG GCAGNCAGAT CCTGGAAAAC GGGAAAGGTT CCGTTCAGGA     60

CGCTACTTGT GTATAAGAGT CAGGT CTA GAG AGA TTG AGC AAG GAG CCA TTG AAG  115
                            Leu Glu Arg Leu Ser Lys Glu Pro Leu Lys
                             1               5                  10

TGG AAA ACT TGG GGN AGC AGA TTG ACA TTC GGA TCC NCG AAA AAG GCG      163
Trp Lys Thr Trp Gly Ser Arg Leu Thr Phe Gly Ser Xaa Lys Lys Ala
                 15                  20                  25

CGT TCC CAG AAG GTT CCG CAT TCT TAC AAC CTA AGT TCC GCC CTC TGG      211
Arg Ser Gln Lys Val Pro His Ser Tyr Asn Leu Ser Ser Ala Leu Trp
             30                  35                  40

TAC GCC AAA TTG CTG AGT TGG TCA ANG ACA TTC CCG GTA AAG TGC GGG      259
Tyr Ala Lys Leu Leu Ser Trp Ser Xaa Thr Phe Pro Val Lys Cys Gly
        45                  50                  55

TGA CAG GGA ACA CTG ATA ACC AGA AAT TGG ACT CTG AAC TGT ATC          304
    Gln Gly Thr Leu Ile Thr Arg Asn Trp Thr Leu Asn Cys Ile
        60                  65                  70

GCTCGAGCAA GAGAACGGAG TGAACCCACC ATCCNCGGGA TTTATCCTGA ATAGAGGCCA    364

GCTTGGCAAG CTCTTCGGCG ACCTNGTGGG GGATAACNCA AAGAGGTGGG GGTCNCAATG    424
```

-continued

```
GCCAANAAGT CCGGNAAATT CNTAAACCCA NCTTGGATTT TTGGGATTGG GNCCAACCTT    484

CTTTNCCCCC CGAAAAAACN TGGGTTTGGG GTTNTCGGNA AGCCNCCCNA TT            536


(2) INFORMATION FOR SEQ ID NO:    4:

     (i) SEQUENCE CHARACTERISTICS:
          (A) LENGTH:                    38
          (B) TYPE:                      amino acid
          (C) STRANDEDNESS:
          (D) TOPOLOGY:                  linear

    (xi) SEQUENCE DESCRIPTION: SEQ ID NO: 4:

Phe Arg Thr Gly Ser Ala Asp Val Glu Pro Tyr Met Arg Asp Ile Leu
 1               5                  10                  15

Arg Ala Leu Ala Pro Val Leu Asn Gly Ile Pro Asn Arg Ile Ser Leu
             20                  25                  30

Ser Gly His Thr Asp Asp
         35


(2) INFORMATION FOR SEQ ID NO:    5:

     (i) SEQUENCE CHARACTERISTICS:
          (A) LENGTH:                    55
          (B) TYPE:                      amino acid
          (C) STRANDEDNESS:
          (D) TOPOLOGY:                  linear

    (ix) FEATURE:
          (D) OTHER INFORMATION:  Xaa in position 2 is unknown;
               Xaa in position 30 is unknown.

    (xi) SEQUENCE DESCRIPTION: SEQ ID NO: 5:

Ile Xaa Glu Lys Gly Ala Phe Pro Glu Gly Ser Ala Phe Leu Gln Pro
 1               5                  10                  15

Lys Phe Arg Pro Leu Val Arg Gln Ile Ala Glu Leu Val Xaa Asp Ile
             20                  25                  30

Pro Gly Lys Val Arg Val Thr Gly Asn Thr Asp Asn Gln Lys Leu Asp
         35                  40                  45

Ser Glu Leu Tyr Arg Ser Ser
     50                  55


(2) INFORMATION FOR SEQ ID NO:    6:

     (i) SEQUENCE CHARACTERISTICS:
          (A) LENGTH:                    55
          (B) TYPE:                      amino acid
          (C) STRANDEDNESS:
          (D) TOPOLOGY:                  linear

    (xi) SEQUENCE DESCRIPTION: SEQ ID NO: 6:

Leu Gln Glu Ala Val Leu Phe Asp Thr Gly Glu Ala Lys Val Leu Lys
 1               5                  10                  15

Asn Ala Glu Thr Leu Leu His Gln Ile Ala Val Leu Leu Gln Thr Ile
             20                  25                  30

Pro Asn Asp Ile Gln Val Glu Gly His Thr Asp Ser Arg Asn Ile Ser
         35                  40                  45

Thr Tyr Arg Tyr Pro Ser Asn
     50                  55


(2) INFORMATION FOR SEQ ID NO:    7:

     (i) SEQUENCE CHARACTERISTICS:
          (A) LENGTH:                    343
```

-continued

```
        (B) TYPE:                     nucleic acid
        (C) STRANDEDNESS:             single
        (D) TOPOLOGY:                 linear

    (xi) SEQUENCE DESCRIPTION: SEQ ID NO: 7:

AGCTCGCTTT ATCGTCCGTG GTAGAAAAAC CTTGAGTGCC AAAGTGCACT TCCCGTGCAT     60

TTTATGTGTT TGATGCCTAA TTTATCGCCA ACCAAACTTT TTTCTTAAAA AAATCGAAAA    120

TTTTTCCTAA AGGATTTAAA AAACGCGCCG TTATAAAAGG TAACTTTGAG AGAACTACTT    180

TGGTTTTCCG AGACGTCGGA AACCGGATAC ATCGGAAAAT CAATTGGAGA AATCACC ATG   240
                                                                Met
                                                                  1

GCA GTG AAT GTA AAT ACC AAC GTC GCA GCA ATG ACA GCT CAA CGT CAT      288
Ala Val Asn Val Asn Thr Asn Val Ala Ala Met Thr Ala Gln Arg His
            5                  10                  15

TTG ACT GGT GCA ACC AAT GCA CAC CAA ACT CCA CTG GAG CGT CTA TCT      336
Leu Thr Gly Ala Thr Asn Ala His Gln Thr Pro Leu Glu Arg Leu Ser
        20                  25                  30

TCA GGC T                                                            343
Ser Gly
    35
```

VIBRIO CHOLERAE MUTANTS WHICH ARE SOFT-AGAR PENETRATION DEFECTIVE AND LACK A FUNCTIONAL CTXA SUBUNIT

This application is a continuation-in-part of U.S. Ser. No. 08/178,055, filed Jan. 6, 1994, now abandoned, and PCT/US93/06270, filed Jul. 1, 1993.

BACKGROUND OF THE INVENTION

The field of invention is *Vibrio cholerae* vaccines.

After more than 100 years of research on cholerae, there remains a need for an effective cholerae vaccine. There have been six pandemics of this disease caused by strains of *V. cholerae* belonging to the "Classical" biotype. The etiological agents of the current (seventh) pandemic belong to the "El Tor" biotype. Recently the seventh pandemic has extended to a new locale, that of South America. Beginning in January of 1991, an epidemic of cholerae resulted in greater than 250,000 cases and over 2,000 deaths in Peru, Ecuador, Columbia, and Chile. In November of 1992, an antigenically distinct, non-01 form of *V. cholerae* emerged in India and Bangladesh and within eight months caused an estimated 500,000 cases and 6,000 deaths. The pandemic potential of this new strain, designated serogroup 0139 synonym "Bengal", seems assured and is a new cause of concern throughout the developing world. These recent experiences underline the need for effective cholera vaccines against disease due to 01 serogroup El Tor biotype of *V. cholerae* and Bengal 0139 serogroup of *V. cholerae*.

The major issues which must be overcome to produce effective cholerae vaccines are safety, stability and a high degree of antigenicity. Because natural infection by and recovery from cholerae induces immunity lasting at least 3 years, much effort has been made to produce live, attenuated cholerae vaccines that, when administered orally, would mimic the disease in its immunization properties, but would not cause adverse symptoms or reactions in the immunized individual (i.e., vaccines which display low reactogenicity). Vaccines of this type involve deletion mutations that inactivate the gene encoding the A subunit of cholerae toxin, a protein which is responsible for most of the diarrhea seen in this disease. See, for example, Mekalanos, U.S. Pat. Nos. 5,098,998 and 4,882,278, and Kaper et al., U.S. Pat. No. 4,935,364, hereby incorporated by reference. While both oral, killed whole cell vaccines and several live, attenuated cholerae vaccines have been developed, the most promising of these provide little protection against the El Tor biotype of *V. cholerae* and probably no protection against the 0139 serotype.

*V. cholerae* only causes disease when colonization of the small bowel occurs. This colonization is also required for the induction of a localized immune response, an important aspect of development of effective vaccines. It is thought that interaction and uptake of bacteria by Peyers patches is the essential step in the localized immune response pathway. Thus, colonization of the intestine can be divided into two distinct steps: 1) interaction with Peyers patches and subsequent immune responses; and 2) interaction with enterocytes and subsequent disease processes (reactogenicity). Although the factors affecting colonization are not well understood, they are believed to include the TcpA pili and motility.

SUMMARY OF THE INVENTION

The invention features nontoxigenic genetically stable mutant strains of *V. cholerae* which are useful as a live, oral vaccines for inducing immunological protection against cholerae. The mutant strains are genetically engineered mutants which lack DNA encoding a functional ctxA subunit and which also have genetic defects causing them to be soft agar penetration-defective. We have found that such mutants have extremely low reactogenicity in both clinical and laboratory tests, yet elicit a strong immune response. As a result, the soft agar penetration-defective strains have the necessary and desirable characteristics of a human vaccine to *V. cholerae*.

By parental strain is meant any strain from which the mutant strain descends. Any number of mutations may be added to the parental strain prior to or subsequent to the introduction of the soft agar penetration-defective mutation.

By soft agar penetration-defective strain is meant a strain lacking the ability to penetrate a media of high viscosity as measured in vitro by swarming on and within agar media which is between 0.25 and 0.45% agar. Mutants which fail to penetrate soft agar are those which will not spread beyond a diameter of 2 mM, most preferably 1 mM, when stabbed or plated by dilution onto soft agar and incubated overnight at 300. Soft agar penetration-defective mutants may be filamentous, motility defective (Mot$^-$), lacking flagella (Fla$^-$), and/or show a decreased ability to bind HEp-2 cells (HEp-2$^-$). The most preferable strains are Mot$^-$ Fla$^+$ HEp-2$^-$, or filamentous.

Filamentous strains are defined as those which appear elongated by microscopic examination, i.e. 25% or more cells appear to be greater than 15 nM in length under conditions of logarithmic growth.

Mot$^-$ Fla$^+$ strains are defined as those strains which have complete flagellum when inspected by electron microscopy, yet remain soft agar penetration-defective and show decreased or non-existent swimming behavior relative to the parent strain when observed in liquid medium. Useful Mot$^-$ Fla$^+$ strains include strains which have disruptions of the motB gene described below or *V. cholerae* homolog of the motA gene from *E. coli*. Most preferably, the soft agar phenotype is caused by a disruption in the motB gene, which causes complete loss of swimming behavior in liquid media, but strains with partial swimming behavior defects may also be useful as vaccines. Mot$^-$Fla$^+$ strains are generally preferable soft agar penetration-defective strains for vaccines because they are penetration defective, yet present all the flagellar antigens as immunogens.

Fla$^-$ strains are defined as those strains which have defective flagellum and are, therefore, soft agar penetration-defective. Useful soft agar penetration-defective strains which are Fla$^-$ may be detected by the observation of incomplete, defective or nonexistent flagellum when evaluated by electron microscope, and by their decreased or non-existent swimming behavior relative to the parent strain in addition to their soft agar penetration-defective phenotype. Useful Fla$^-$ phenotypes may be obtained by the disruption of the *V. cholerae* homologs of the fliC, fljB, flhC, flhD, fliA, flgM, fliS, flit, fliD, fljA, flhA, fliH, fliI, flgA, flgD, fliK, fliB, flig, flim, flin, flIF, fliE, flgB, flgC, flgF, flgG, flgI, flgH, flgE, flgK, flgL, fliD, figj, flhB, flhE, fliJ, flil, fliO, fliP, fliQ, fliR of *E. coli, S. typhimurium*, species Bacillus, *V. parahaemolyticus*, species Helicobacter, *C. crescentus, P. mirabilif*, and *B. Pertussis* (listed in order of preference, see Table 1, below), for example. Most preferably, the disruption is a disruption of the fliC gene of *V. cholerae* described herein a disruption of the motility gene or genes which are disrupted or the disruptions present in the Bengal-15, Peru-14, Peru-15, Bah-15, and Bang-15 strains.

TABLE 1

| Flagellar and motility gene products of *S. typhimurium* and *E. coli* and their known or suspected functions | |
|---|---|
| Gene product | Function/location |
| Regulatory proteins | |
| FlhC, FlhD | Master regulators of the flagellar regulon acting on class 2 operons. Transcription initiation (σ) factors? |
| FliA | Transcription initiation (σ) factor for class 3a and 3b operons. |
| FlgM | Anti-FliA (anti-σ) factor. Also known as RflB. Active only when flagellar assembly has not proceeded through completion of the hook. |
| FliS, FliT, FliD? | Repressor of class 3a and 3b operons (RflA activity) |
| FljA | Repressor of fliC operon. |
| Hin | Site-specific recombinase, affecting fljB promoter. |
| Proteins involved in the assembly process | |
| FlhA, FliH, FliI | Export of flagellar proteins? FlhA is homolog of various virulence factors. FliI is homolog of the catalytic subunit on the $F_0F_1$ ATPase. |
| FlgA | Assembly of basal-body periplasmic P ring. |
| FlgD | Initiation of hook assembly. |
| FliK | Control of hook length. |
| FliB | Methylation of lysine residues on the filament protein, flagellin; function of this modification unknown. |
| Flagellar structural components | |
| FliG, FliM, FliN | Components of flagellar switch, enabling rotation and determining its direction (CCW vs CW). FliM is also implicated as a signalling protein. |
| MotA, MotB | Enable motor rotation. No effect on switching. |
| FliF | Basal-body MS (Membrane and Supramembrane) ring and collar. |
| FliE | Basal-body component, possibly at (MS-ring)-rod junction. |
| FlgB, FlgC, FlgF | Cell-proximal portion of basal-body rod. |
| FlgG | Cell-distal portion of basal-body rod. |
| FlgI | Basal-body periplasmic P ring. |
| FlgH | Basal-body outer-membrane L (Lipopolysaccharide layer) ring. |
| FlgE | Hook. |
| FlgK, FlgL | Hook-filament junction. |
| FliC, FljB | Filament (flagellin protein). FljB (found in *S. typhimurium* only) is an alternative, serotypically distinct, flagellin. |
| FliD | Filament cap, enabling filament assembly. |
| Flagellar proteins of unknown function | |
| FlgJ, FlhB, FlhE, FliJ, FliL, FliO, FliP, FliQ, FliR. | |

Strains which are HEp-2$^-$ are defined as those strains which show a 5-fold or greater decrease in binding to HEp-2 cells relative to the non-soft agar penetration-defective mutant parent strain in the assay provided below.

By a ctxA subunit is meant the A subunit of the *V. cholerae* toxin which is responsible, when functional, for many of the symptoms of cholerae (e.g., nausea, diarrhea etc.). Most preferably, the strains include deletion of the entire so-called "core genetic element", which includes not only the ctxA/B, but also a region known as icf (encoding Intestinal Colonization Factor, probably equivalent CEP "core encoded pilin") and zot, described in greater detail below. In preferred embodiments the strain is also att$^-$.

The method by which the vaccine strains of the invention are made includes introducing a mutation causing a soft agar penetration-defective phenotype into a *V. cholerae* strain containing a mutation in the ctxA sequences. The *V. cholerae* soft agar penetration-defective mutation preferably shows a reversion frequency of less than $1\times10^{-9}$ mutant cells. Soft agar penetration-defective mutations may be isolated as spontaneous mutants or by genetic engineering of genes identified by transposon mutagenesis or by homology to genes previously identified in another enteric bacteria such as *E. coli, S. typhimurium*, species Bacillus, *V. parahaemolyticus*, species Helicobacter, *C. crescentus, P. mirabilif*, and *B. Pertussis*. Preferably, the gene identified by homology is one of the Fla, Mot or Che genes in Table 1, above. Most preferably the gene is either MotB or FliC.

The desruptions may be spontaneous mutation or may be genetically engineered deletions.

In some cases it will be preferable to use standard techniques of molecular biology to map spontaneous mutations in soft agar defective penetrations strains (i.e., in Peru-14, Peru-15, Bengal-15, Bang-15 or Bah-15). Once mapped, the gene bearing the mutation (or its non-mutant homolog) may be fully or partially deleted to make a stable, non-reverting vaccine strain. The invention provides parental strains and methods for use in making such genetically engineered soft agar penetration defective vaccine strains.

Although any serotype of *V. cholerae* parent strain may be used in the method, in preferred embodiments the mutant strain of *V. cholerae* belongs to the El Tor biotype, and, more preferably, the Inaba or Ogawa serotype or belongs to the *V. cholerae* non-01 serogroup, preferably 0139 "Bengal" serogroup. Preferably, the mutants lack all of the CTX core and attRS1 sequences and, more preferably, the mutant strain is a derivative of Peru-2, Bang-2, or Bah-2 serotypes, or an attenuated derivative of the Bengal serotype, such as Bengal-2 ("Beng-2") or Bengal-3 ("Beng-3") as described below.

Mutant strains according to the invention optionally include additional mutations introduced to improve the safety and/or the immunogenicity of the vaccine. Such additional mutations include, but are not limited to, inactivation of one or more genes involved in DNA recombination, for example the recA gene encoded by the strain. In addition, genes may be introduced into the *V. cholerae* chromosome, preferably into the *V. cholerae* lacZ gene, to provide immunogenicity to heterologous antigens. Preferably, the mutant strain including additional mutations is Peru-14, Peru-15, Bang-15, Bengal-15 or Bah-15, or a soft agar penetration-defective derivative of Peru-2, Peru-3, Bang-2, Bang-3, Bah-2, Bah-3, Bengal-2, or Bengal-3, or the genetic equivalents thereof.

By genetic equivalent is meant any strain having the same combination of ctxA/B, attRS1, recA, and icf mutations as are present in the stated strains.

Because the Mot$^-$ soft agar penetration-defective strains show increased constitutive expression of toxin, Tcp pili and hemolysin proteins, the strains may also be used in the manufacture of killed vaccine substrates.

In preferred embodiments, the invention includes a vaccine comprising at least two different strains of *V. cholerae* which are nontoxigenic genetically stable mutants which lack DNA encoding a functional ctxA subunit and are also soft agar penetration-defective. One of the two strains is preferably derived from an El Tor 01 strain and the other one is derived from a Bengal strain. More preferably, one of the serotypes in the El Tor 01 component of the vaccine is an Ogawa serotype or an Inaba serotype. Most preferably, the vaccine includes Peru-15 and Bengal-15 as Peru-14 and Bengal-15.

Most preferably, the live or killed oral vaccine comprises at least two vaccine strains chosen from the soft agar penetration-defective derivatives of Bah-3, Peru-3, Bang-3 and Bengal-3. Most preferably, the live vaccine includes Peru-15 and either Bengal-15 or strains bearing genetically engineered deletions of the genes conferring the soft agar penetration-defective phenotypes present in these strains. The preferable killed vaccine contains one strain of each of the serotypes Ogawa and Inaba and one strain of the Bengal serotype. The most preferable killed vaccine contains Peru-15, Bah-15 and Bengal-15 or strains bearing genetically engineered deletions of the genes conferring the soft agar penetration-defective phenotypes present in these strains.

Depending upon the relevant local epidemiology, the vaccine strains may be administered together in a single dose, or, more preferably, separately 7–28 days apart. Where only one of the serotypes presents a threat of disease, it may be preferable to administer a vaccine regimen comprising only one strain.

Strains such as those described above are useful as cholerae vaccines and are improved in their genetic properties compared with previous vaccines.

Other features and advantages of the invention will be apparent from the following description of preferred embodiments thereof, and from the claims.

DETAILED DESCRIPTION

The drawings will first be briefly described.

The Drawings

FIG. 1 is a photograph showing soft agar penetration-defective and soft agar penetrating strains in a soft agar penetration assay. A14456, left, is a wild-type *V. cholerae* serotype 0139 strain; A14456 Sm, middle, is a streptomycin resistant isolate of A14456; and VR1-16, right, is a derivative of A14456 which has an attRS1 deletion.

FIG. 4 is the sequence of *V. cholerae* motB (SEQ ID NOS:3 and 5) and related sequences from *E. coli* (SEQ ID NO:4) and *B. subtilis* (SEQ ID NO:6).

FIG. 5 is the sequence of *V. cholerae* fliC gene (SEQ ID NO: 7).

Figure 1:
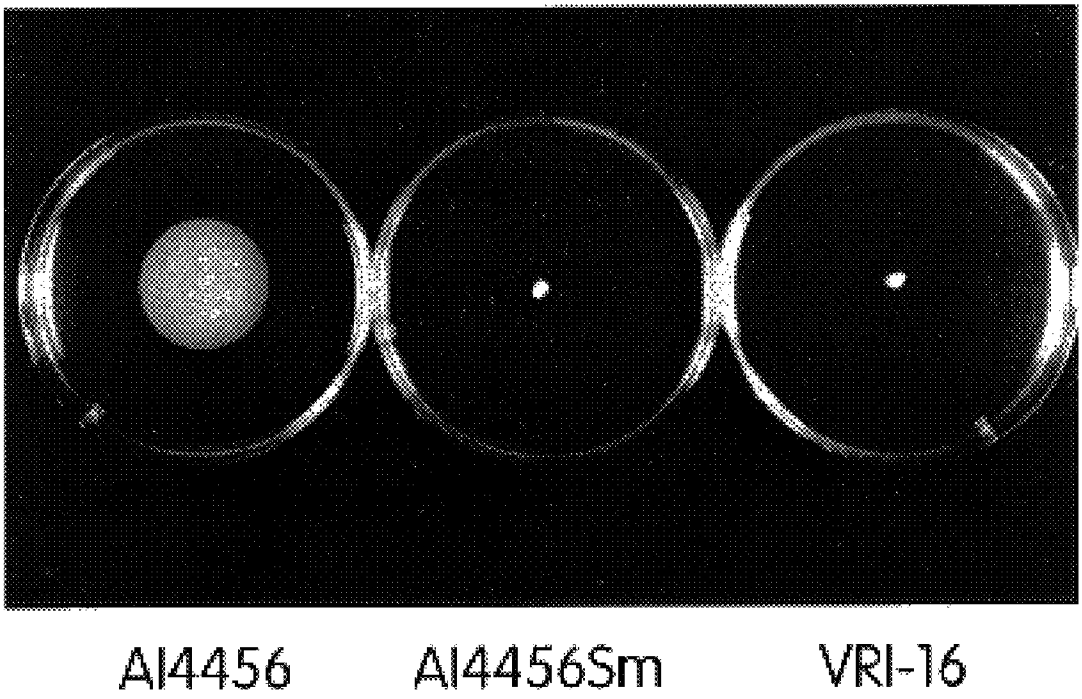

The invention features attenuated strains of *V. cholerae* that can be used as live oral vaccines to protect individuals against cholerae and potentially other diseases.

We have discovered that *V. cholerae* strains which are soft agar penetration-defective have surprisingly low reactogenicity when compared with soft agar penetrating strains. Nonetheless, these strains have strong immunogenicity. We believe these vaccines may interact strongly with Peyers patch tissue without interacting strongly with entrocyte epithelium. When combined with disruptions of the ctxA gene, the soft agar penetration-defective mutations result in strains which are excellent vaccines for the prevention of cholerae in humans.

Without wishing to bind ourselves to a specific theory, we believe that the low reactogenicity of these strains stems from their inability to penetrate the mucosa of the intestine. The mucous layer of the intestine is thought to be viscous and mutants defective in penetration of soft agar might be deficient in penetration of this mucous. Although defective in penetration through mucous, these mutants may still present antigen to the Peyer patches, which are not covered by a thick mucous gel. Localization to the Peyer patches is important for an effective vaccine because the patches include antigen-sampling cells specific for IgA antibody production. As a result, penetration defective mutants are predicted to generally have low reactogenicity, yet be highly antigenic. We have constructed both filamentous and non-motile mutant vaccines which demonstrate these features (see Examples 1–6, below). $Mot^-Fla^+$ mutants are one class of mutants defective in penetration of soft agar, however, other types of mutants, such as filamentous and $Fla^-$ mutants, also result in a soft agar penetration-defective phenotype (i.e., a non-swarming phenotype) and may be useful for vaccines.

Although decreased mucosal penetration is likely tobe the primary reason for the success of the soft agar penetration-defective vaccines, we have also found that $Mot^-$ strains display increased constitutive expression of toxin, Tcp pili and hemolysin genes. This increased expression may account for the enhanced immunogenicity of these strains. Paradoxically, the increased production of the Tcp pili does not cause increased reactogenicity; it may be that Tcp pilus-mediated adherence to the mucosa in these strains is of a nature which is either less disruptive to gut physiology or is dependent on a step which first requires motility to deliver the organisms to Tcp host receptors.

I. METHODS OF CONSTRUCTING SOFT AGAR PENETRATION-DEFECTIVE VACCINES

Parental *V. cholerae* strains.

Provided below in Table 2 is a list of strains which may be used to isolate soft agar penetration-defective mutants which are useful vaccines. This table is not meant to be limiting, but rather is meant to provide examples of the types of strains which may be employed.

TABLE 2

STRAINS FOR VACCINE CONSTRUCTION

| Strain | Serotype | Relevant* Genotype |
|---|---|---|
| Peru-2 | Inaba | Type-2 CTX deletion, str |
| Peru-3 | Inaba | attRS1 deletion, recA::htpP-ctxB, str |
| Peru-4 | Inaba | Type-2 CTX deletion recA::ctx-ctxB |
| Peru-5 | Inaba | attRS1 deletion, lacZ::ctxP-ctxB, str |
| Bang-2 | Ogawa | Type-2 CTX deletion, str |
| Bang-3 | Ogawa | attRS1 deletion, recA::htpP-ctxB, str |
| Bang-5 | Ogawa | attRS1 deletion, lacZ::ctxP-ctxB, str |
| Bah-2 | Inaba | Type-2 CTX deletion, str |
| Bah-3 | Inaba | attRS1 deletion, recA::htpP-ctxB, str |
| Bah-5 | Inaba | attRS1 deletion, recA::ctxP-ctxB, str |
| Bengal-2 | Bengal | Type-2 CTX deletion, str |
| Bengal-3 | Bengal | attRS1 deletion, recA::htpP-ctxB, str |
| Bengal-4 | Bengal | Type-2 recA::ctx-ctxB |
| Bengal-5 | Bengal | attRS1 deletion, recA::ctxP-ctxB, str |

*Note str under relevant genotype refers to streptomycin resistance. This is a spontaneously mutated strain is resistant to 100 μg/ml of streptomycin as a result of a mutation in a ribosomal protein. All strains and the methods for making the same are described in Mekalanos, U.S. Ser. No. 08/083, 388, filed June 28, 1993. The parent strains are C6709-Sm (Peru-2), P27459-Sm (Bang-2), and E7946-Sm (Bah-2).

Construction of Vaccines with additional mutations.

In addition to the soft agar penetration-defective and ctxA mutations, the desirable vaccine may contain other mutations known to improve vaccine safety, reactogenicity and immunogenicity. The following are examples of useful mutations which may be employed.

attRS1 deletions. In addition to having low reactogenicity, genetically engineered live attenuated cholerae vaccines are theoretically safe only if they cannot revert or otherwise regain the capacity to produce cholerae toxin. Strains which carry a single copy of the attRS1 sequence can efficiently acquire a new copy of the CTX element through DNA transfer by either P factor conjugation or bacteriophage transduction. Thus, deletions which render *V. cholerae* devoid of RS1 and attRS1 sequences can prevent a vaccine strain from reacquiring the CTX genetic element in nature through its own site specific recombination system. Methods of making RS1 and attRS1 deletions and parental vaccine strains containing these mutations are described in Mekalanos, U.S. Ser. No. 08/083,388, filed Jun. 28, 1993, incorporated herein by reference. For example, Peru-3, Bang-3, Bah-3 and Bengal-3 have these deletions and may be used as parental starting strains in the methods of the invention.

$Rec^-$ Mutations. The mutant strains described can be further improved as vaccine candidates by creating additional mutations within each strain that will serve to enhance the safety and immunogenicity of the vaccine.

With regard to safety, an additional mutation can be introduced into the recA gene of any of the strains described, which mutation is designed to inactivate that recA gene. Such double mutant strains will therefore be defective in recombination and will be unable to recombine with wild type strains of *V. cholerae* in the environment. Thus, they will be incapable of acquiring wild type toxin genes and expressing the CTX element.

Thus, a series of mutated derivatives can also be useful in the invention, each incorporating additional properties that render the strains safer, genetically more stable and more broadly immunogenic. The construction of such derivatives is described in Mekalanos, U.S. Ser. No. 08/083,388, filed Jun. 28, 1993.

icf and zot mutations. Recently, a new toxin called ZOT has been found to be encoded by the core region (Baudry et al., 1992, Infect. Immun. 60:428–434). In addition, we have previously found evidence that Type-1 or Type-2 CTX deletion mutants described in Mekalanos, U.S. Ser. No. 08/083,388 filed Jun. 28, 1993, have decreased colonization and, therefore, enhanced vaccine characteristics. The gene deleted which causes decreased colonization is called icf (or "cep") and encodes ICF. Icf is separate and distinct from zot and both may be useful in the preferred soft agar penetration-defective vaccine. Strains in Table 2 ending in "-2", "-4" and "-5" (e.g., Beng-2) contain the icf deletion and may be used as parental starting strains in the methods of the invention. In addition, the soft agar penetration-defective strains in Examples 2, 3 and 4 also contain icf deletions.

Isolation of spontaneous soft agar penetration-defective mutations of *V. cholerae.*

To obtain spontaneous soft agar penetration-defective mutants, soft agar can be used to assess the ability of bacteria to penetrate a media of high viscosity (soft agar media which is 0.25–0.45% agar). Spontaneous soft agar penetration-defective vaccines with a high therapeutic value include Peru-14, Peru-15, Bang-15, Bah-15, and Bengal-15 (see Example 3, below).

Spontaneous soft agar penetration-defective strains may be isolated from any *V. cholerae* parent strain using the following method. *V. cholerae* cells are grown to stationary phase in test tubes in Luria broth (LB) without agitation (or are grown on LB plates) at 300 for 24–48 hours. The *V. cholerae* cells are then collected from the bottom of the test tube (or off the plate) and recultured by repeating the stationary 300 growth conditions. After the second cycle of growth cells are serially diluted sufficient to give one cell/1μl and plated within 0.4% soft LB agar (100 μl/plate) or repicked off the LB plate, onto soft agar if using the plate method. Plates are then incubated at 300 overnight (12–30 hours). Soft agar penetrating cells will give rise to spreading colonies, while soft agar penetration-defective mutants will yield pinpoint colonies of less than 2 mM. Cells from pinpoint colonies are then stabbed onto new soft agar plates. Those stabs which yield pinpoint colonies and not give rise to revertants (spreading cells) are useful soft agar penetration-defective mutant strains (for example, see FIG. 1).

Isolation of soft agar penetration-defective mutants by transposon mutagenesis.

Figure 2:
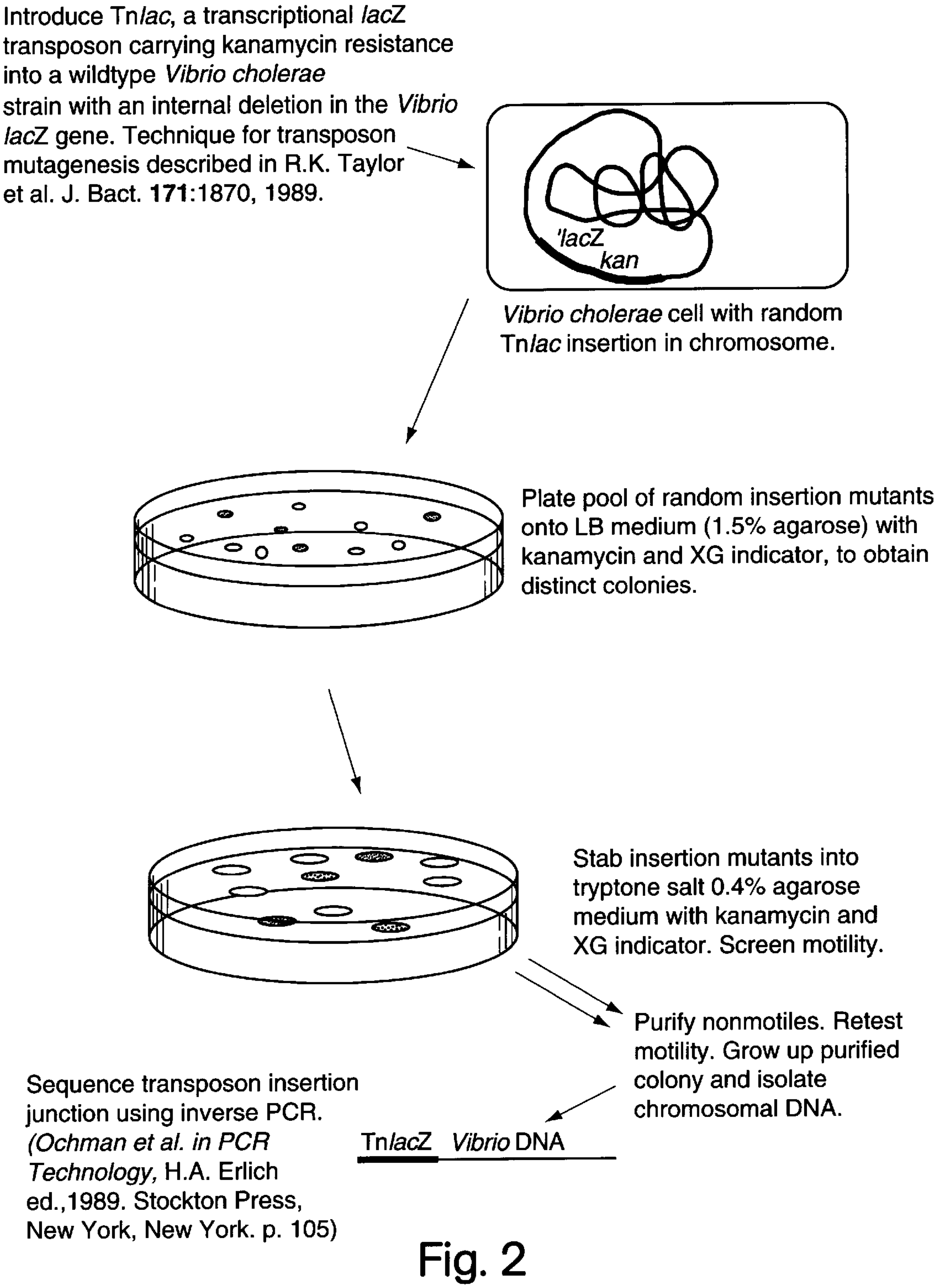
FIG. 2 is a schematic diagram of the method used to isolate soft agar penetration-defective mutants using transposon mutagenesis.

Transposon mutagenesis allows the identification, sequencing, cloning and characterization of soft agar penetration-defective mutants without requiring any prior knowledge of the gene sequence, chromosomal location, etc. Furthermore, any gene useful for construction of soft agar penetration-defective vaccines may potentially be isolated using this technique. In addition, this technique allows an assessment of the nature of the soft agar penetration-defective phenotype prior to cloning, sequencing, etc., thereby minimizing laboratory effort required to construct vaccines. The protocol for transposon mutagenesis is depicted in FIG. 2. The technique is described in Taylor et al., *J. Bact.* 171:1870 (1989). Briefly, a transcriptional lacZ transposon carrying kanamycin resistance, is introduced into a soft agar penetrating parent *V. cholerae* strain which has an internal deletion of the lacZ gene. The transposon integrates randomly and integrants may be selected on LB media plates (1.5% agarase) with Kanamycin and XG indicator (5-bromo-4-chloro-3-indolyl-β-D-galactoside, Boehringer Mannheim, Indianapolis, Ind.). Cells from Kanamycin resistant colonies are then individually stabbed onto 0.4% agarase medium, with Kanamycin and XG indicator. Integrants with a soft agar penetration-defective phenotype are readily identified as non-spreading colonies (see below FIG. 1). Soft agar penetration-defective colonies are then purified, retested, and chromosomal DNA is isolated. The transposon insertion junction may be sequenced, and the parent gene identified using inverse PCR (Lochman et al., in *PCR Technology*, H. A. Erlich ed., 1989. Stockton Press, N.Y., N.Y. p. 105). Oligomeres useful for PCR sequencing are provided in Example 5, although other oligomeres may be readily synthesized and utilized using standard techniques. Once sequencing is performed the disrupted gene may be identified by homology to known enteric motility genes (see Table 2, below).

We have used this method to identify motB in cholerae (see Example 5). Once the gene conferring the desirable phenotype has been identified a knockout mutation which does not confer drug resistance may be generated using standard genetic engineering techniques, for example, those provided below.

Isolation of soft agar penetration-defective mutants by disruption of genes identified by homology cloning The sequences of many genes encoding proteins necessary for mobility of enteric bacteria and thus penetration through soft agar are known. Because *V. cholerae is so closely related (see Examples* 5 and 6) to these enteric bacteria these sequences may be used to design degenerate oligonucleotides which may, in turn, be used to either sequence the *V. cholerae* homology by PCR or to isolate a clone bearing the gene from a *V. cholerae* DNA library. If sequenced by PCR, the resulting sequence may be used to isolate a clone bearing the gene from a *V. cholerae* library. Using either method, a disruption of the gene by insertion or deletion may be made using standard molecular biology procedures (see Example 6) and the resulting mutant gene recombined into the vaccine strain. Example 6 provides an additional cloning scheme which may be used to detect genes which may be mutated to confer SAP-D phenotypes.

II. CHARACTERIZATION OF SOFT AGAR PENETRATION-DEFECTIVE MUTANTS

Assay for flagella by electron microscope.

The presence or absence of flagella may be detected using an electron microscope and standard procedures, with the following protocol modifications. 50 μl of a mid log phase or diluted stationary phase culture are placed in an inverted small plastic test tube cap. Tweezers are then used to place a piece of carbon-coated mica into the drop until the carbon lifts off and carbon is then caught on the mica and lifted into an inverted cap (from a Falcon 15 ml tube) full of stain (either 1% uranyl phosphate or 0.5% molybdenate.) Mica is allowed to fall to bottom of cap while carbon floats on surface. Floating carbon is picked up with small round copper grid and carefully blotted dry with Whatmann filter paper. The sample is then observed in the electron microscope and scored for the presence or absence of flagella.

Assay for HED-2 adherence.

HEp-2 cells are commercially available from the ATCC, Bethesda, Md. (ATCC CCL23). Adherence may be determined relative to the parent-strain using the following protocol. *V. cholerae* cultures are grown overnight with aeration (in Rolodrum) in 5 mls LB at 30° C., then subcultured 1/100 and incubated at 30° C. with aeration for approximately 2 hrs until the bacteria have reached midlog phase. *V. cholerae* cells are then washed 2 times in PBS (phosphate buffered saline) to remove any toxin. To achieve a multiplicity of infection (MOI) of 100, bacteria are added to wells with small round glass coverslips seeded with approximately $10^5$ HEp-2 cells in IMEM media with 5% fetal bovine serum and glutamine (2 mM) without antibiotics. *V. cholerae* cells are then spun down at 1000 rpm in desktop centrifuge for 10 minutes and *V. cholerae* cells and HEp-2 cells are incubated for 20 minutes at temperature or 30° C. Suction is then used to remove fluid in wells and cells are washed by adding 1 ml of PBS to each well, followed by suction removal. This washing is repeated 3 additional times. The slide is then fixed in methanol for 5 minutes at room temperature and then methanol is removed completely by suction. Giemsa stain is added in a 1/12.5 dilution in $H_2O$ to each well and slides are allowed to sit for 25 minutes. Stain is then removed by suction and wells are washed 4 times with PBS. Coverslips are then removed and slides are placed cell side up on paper towel and air dried. Coverslips are mounted cell side down onto glass slides using Pro-texx Mounting medium and allowed to set overnight. Cells are then observed and adherent bacteria are counted using light microscope.

Serological Characterization of Vaccine Strains.

Each derivative may be demonstrated to retain its expected serotype (i.e., the serotype of each of the mutants respective parental strain) by testing freshly harvested bacterial cells by slide agglutination using Difco *V. cholerae* 01 Inaba or Ogawa typing serum or 0139 specific typing serum. We have tested all *V. cholerae* vaccine strains specifically described herein and these tests indicate that the strains still express the appropriate LPS antigens. Other tests may be used to demonstrate that mutant strains are prototrophic and still express Tcp pili (e.g., see Example 1). Thus, the mutants may be shown to express a number of properties that are important for their ability to be useful as live vaccine strains.

Colonization Properties of the Vaccine Strains.

To test the colonization properties of these vaccine strains, a mouse intestinal competition assay may be used as described in Taylor et al. (Proc. Natl. Acad. Sci. USA. 84:2833–2837, 1987). This assay has been shown to yield results which correlate accurately with the colonization properties of mutant strains when they are subsequently tested in human volunteers (Herrington et al., *J. Exper. Med.* 168:1487–1492, 1988). The assay measures differences in colonization of a mutant strain by comparing its ability to compete for growth and survival with another closely related or isogenic strain. In this assay, the mutant and competing strains are mixed in a ratio of approximately 1:1 and then approximately one million cells of this mixture are introduced to the stomach of 3–5 day old suckling CD-1 mice. After 24 hours, the mice are sacrificed, the intestine was dissected, homogenized, and plated on bacteriological media containing an antibiotic which selects for both the strains. Colonies that grow after overnight incubation are then tested for additional markers which differentiate the mutant strain from the competing strain (i.e., resistance to kanamycin or hybridization with appropriate radioactive DNA probes).

Suckling mouse colonization assay.

Ratio of the fluid in the intestinal loops (ml) to the length (cm) (the FA ratio) may be determined as described by Baselski et al., *Infect. Immun.* 15:704–712 (1977). Briefly, mice are inoculated with $2.5\times10^6$ to $6.0\times10^8$ CFU, as determined by plating dilutions of the inoculum on L agar. Both Swiss Webster (CFW) mice and CD-1 mice may used for FA ratio determination.

The upper halves of the bowels from six to eight mice are pooled and homogenized with an Omni-Mixer, and the CFU per milliliter for each strain was determined by plating dilutions to appropriate antibiotic-containing L-agar plates. For determination of in vivo growth, the entire intestine is homogenized. The output ratio is then calculated.

III. METHODS OF ADMINISTERING SOFT AGAR PENETRATION-DEFECTIVE VACCINES

Use of the Live Vaccine Strains Vaccines derived from *V. cholerae* mutant strains Peru-1, Peru-2, Bang-1, Bang-2, Bah-1, Bah-2, Bengal-2, Bengal-3, or any of the additional mutants described herein are useful as sources of immunological protection against cholerae and other related toxigenic diseases when used as live vaccines. Other such diseases include, but are not limited to, those induced by enterotoxigenic *E. coli* and other bacteria that produce toxins which are immunologically cross-neutralizable with cholerae B subunit.

When inoculated into the intestine of an experimental animal or human, mutant strains of *V. cholerae* should stimulate and induce a strong immunological response against all bacterial components that are elaborated by these strains including, but not limited to, the Ogawa and Inaba serotype 01 serogroup LPS antigens, flagella antigens, the antigenic domains of the Tcp pili, and the outer membrane proteins. Based on published studies with other prototype cholerae vaccines, both IgA and IgG classes of antibodies directed against these bacterial components will be synthesized in the inoculated animal or human and will serve to protect the animal or human against subsequent challenge with virulent strains of *V. cholerae.*

Dosage

Determination of the appropriate dosage and administration of these vaccines is performed essentially as described in Herrington et al., (1988, J. Exper. Med. 168:1487–1492). In general, such dosages are between, but are not limited to, $10^5$–$10^9$ viable bacteria per dose.

Growth of Vaccine Strains

The bacteria to be used as the vaccine can be grown in a standard *V. cholerae* laboratory media. The cells can be harvested and then lyophilized in a formulation that preserves viability (e.g., sterile skim milk or saline containing 5 mM $CaCl_2$ and 10% weight by volume of glycerol).

Administration

Administration of the vaccine involves combining the contents of two envelopes or vials, one containing the lyophilized vaccine strain or combination of strains, the other containing water and sufficient sodium bicarbonate or alternate buffer as to neutralize stomach acid (approximately 2 grams). The vaccine can then be swallowed by the vaccinee. Alternatively, the lyophilized vaccine can be incorporated into tablets which can be coated with an acid resistant "enteric coating". Such a form of vaccine can be administered to the vaccinee in one or more (up to three) doses spaced from a few days to several weeks apart. When used as a "booster" vaccine, the vaccine can also be administered to previously vaccinated individuals in one or more doses (up to three) spaced from a few days to several weeks apart. When two or more strains are being administered they may be provided together, or in individual doses 7–28 days apart.

IV. EXAMPLES

The following examples are provided to illustrate not limit the invention.

Example 1

General features of motility and chemotaxis defective mutants

In order to determine the effects of motility on the expression of virulence factors, motility and chemotaxis mutants were isolated. Both spontaneous and transposon-induced mutants with altered swimming patterns were obtained. Spontaneous soft agar penetration-defective (nonmotile) and hypermotile mutants were obtained, as were insertion induced soft agar penetration-defective mutants. Mutants were examined for cholerae toxin production, TCP expression, hemagglutination, hemolysis, adherence to HEp-2 cells, and ability to colonize infant mice.

Figure 3:
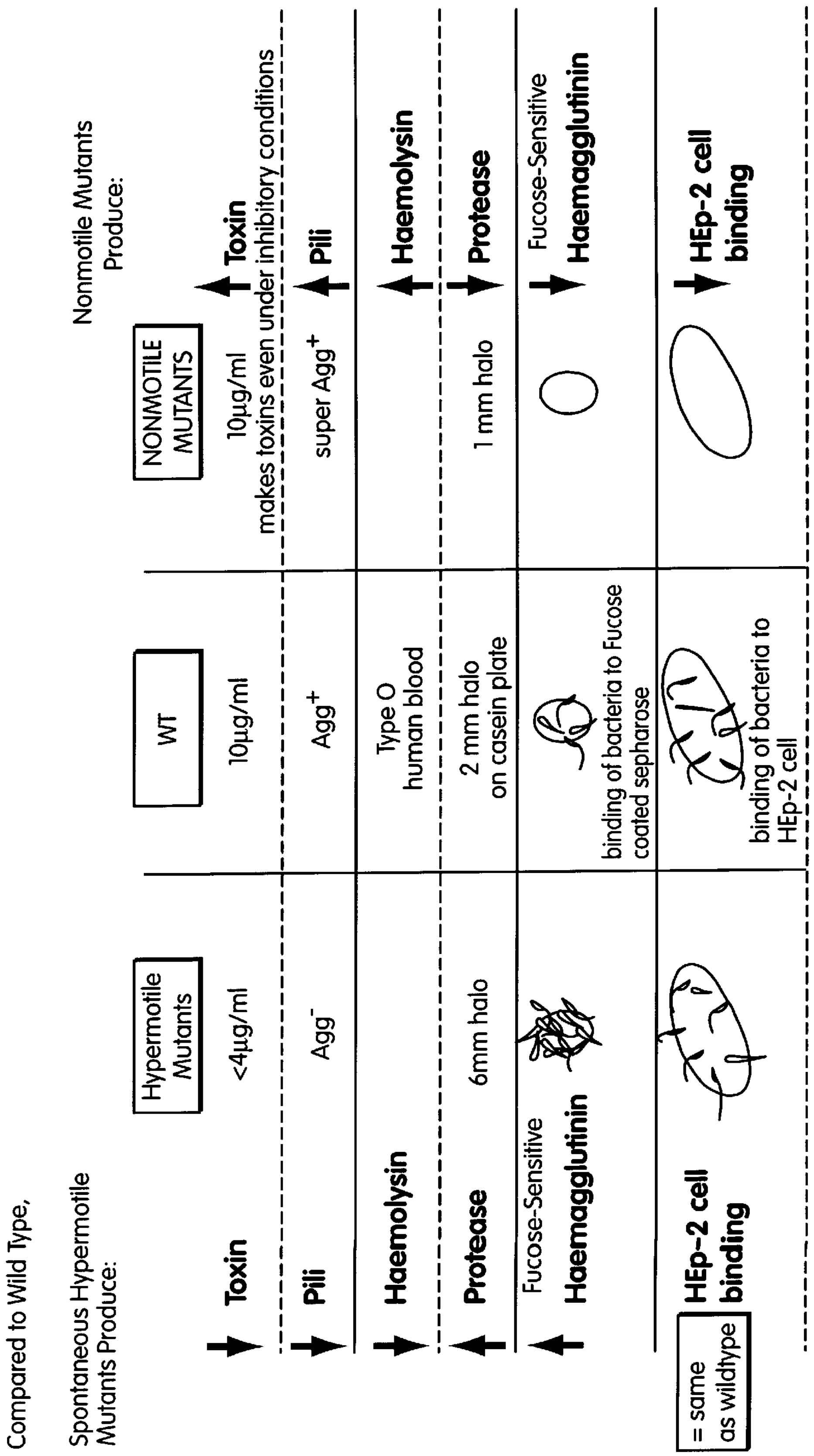
FIG. 3 depicts the general characteristics of spontaneously isolated hypermotile, wild-type and non-motile mutants.

In general, hypermotile mutants were defective in toxin and TCP production while nonmotile mutants showed increased toxin and TCP expression. These results suggest that virulence and motility are oppositely regulated. Although nonmotile mutants make TCP, they are unable to bind HEp-2 cells (see FIG. 3). Addition of agents that inhibit motility of wild-type bacteria were also found to abolish adherence to HED-2 cells, suggesting that motility itself is required for binding.

In vivo competitions between the mutants and wild-type *V. cholerae* in the infant mouse model reveal that both classes of mutants are dramatically attenuated. These colonization defects exhibited by the hypermotile and soft agar penetration-defective mutants may result from theabsence of toxin and TCP, the lack of adherence and motility, or the inability to reach the intestinal epithelium.

Example 2

Isolation filamentous mutants by spontaneous mutagenesis.

Peru-14 is soft agar penetration-defective, and, in addition, over 50% of Peru-14 cells are filamentous, with a spiral-like appearance and having a cell length of greater than 5 normal cell lengths (25 nM, as opposed to the wild-type cells length of 5 nM).

Peru-14 was isolated as a spontaneous soft agar penetration-defective derivative of the triply-deleted Peru strain (Peru-3, $ctxA^-$, $att^-$, and $recA^-$) that was free from side effects but still retained the ability to colonize and act as a vaccine, as shown in below (Tables 3 and 4).

Although Peru-14 was isolated based upon the theory stated above, this theory of function may or may not accurately and completely explain the effectiveness of Peru-14 as a vaccine. The usefulness of Peru-14 (or any other vaccine described herein) as an effective vaccine does not depend on the correctness of this theory.

TABLE 3

Outcome of Immunization with Freshly Harvested Peru-14 Cholerae Vaccine

| Dose (cfu) | Volunteer # | Symptoms | Stool | Duration of Excretion (days)/Peak day |
|---|---|---|---|---|
| $2 \times 10^6$ | 28 | Gas | Formed | 3/3 |
| | 29 | Cramps | Formed | 4/2 |
| | 30 | None | Formed | — |
| | 33 | None | Formed | 4/4 |
| | 34 | None | 336 g* | 4/1 |
| | 35 | None | Formed | 3/3 |
| $9 \times 10^8$ | 25 | None | Formed | 5/1 |
| | 26 | Gas | Formed | 3/1 |
| | 27 | Headache | Formed | 2/2 |
| | 31 | Nausea, Loss of Appetite | Formed | 7/4 |
| | 32 | None | Formed | 5/3 |
| | 36 | Cramps | 63 g+ | 3/1 |

*Volunteer had painless semi-solid stool at 72 hours post-immunization. Stool was culture-negative for Peru-14.
+Volunteer had two small liquid stools at 48 hours post-immunization. Stools were culture-positive for Peru-14.

TABLE 4

Comparison Reactogenicity with differing El Tor01 Vaccine Strains

| Strains | No. with diarrhea | No. with significant other symtoms[1] |
|---|---|---|
| Motile Strains | 2/3 | 3/3 |
| Bah-3 | 1/3 | 3/3 |
| Bang-3 | 1/3 | 2/6 |
| Peru-3 | 2/6 | 2/6 |
| Motility-Deficient Strain[2] Peru-14 | 1/21 | 2/21 |

[1]Moderate to severe abdominal cramps, malaise, emesis, or fever.
[2]Peru-14 is a filamentous mutant of Peru-3 and is motility-deficient Specifically, the Peru-14 soft agar penetration-defective strain was produced as follows. Peru-3 was grown overnight in LB broth containing 100 μg streptomycin sulfate at 30° C. The culture was diluted to approximately 2000 cfu/ml and 0.1 ml was plated onto LB plates containing 100 μg streptomycin. After incubating the plates overnight at 30° C., approximately 1000 colonies were toothpicked into soft agar plates (LB broth+0.45% Bacto-agar) and incubated overnight at 30° C. The inoculating toothpick is inserted only 1–2 mm into the surface of the soft agar plate. Of the 1000 colonies picked, 25 appeared to be non-penetrating. Non-penetrating isolates appear as colonies of approximately 2 mm in diameter, whereas penetrating isolates swarm on and within agar the agar to a diameter greater than 5 mm. These colonies were repicked into soft agar once again, along with a known non-penetrating, non-motile cholerae strain and the original Peru-3 strain. One colony of the 25 was non-soft agar penetrating (when compared to the controls). This colony, designated Peru-14, was still Inaba positive with agglutination sera, and produced the same level of B-subunit toxin as Peru-3 when tested in the B-subunit ELISA. The methods described above can be used for isolating soft agar penetration defective mutants of any *V. cholerae* strain. Non-revertible penetration-defective mutants, such as those harboring a genetic deletion, can be made using the methods described above.

Example 3

Isolation of spontaneous mutations which are soft agar penetration-defective and $Mot^-$.

The spontaneous mutant isolation protocol described generally above has been used to isolate soft agar penetration-defective of Peru-2, Bang-2 and Bah-2 (all $Rec^+$) Peru-3, Bah-3 and Bang-3, and Bengal-3 (all $Rec^-$). All are $Mot^-$ $Fla^-$ by the electron microscopic assays. $Rec^-$ derivatives of Peru-3, Bah-3, Bang-3 and Bengal-3 are termed Peru-15, Bah-15, Bang-15 and Bengal-15, respectively, and have been further characterized. The results of the mouse colonization assays are shown in Table 6, below. All three strains showed a decrease in colonization relative to the soft agar penetrating parent strain.

Isolation of Peru-15

Peru-15 is a live attenuated oral cholera vaccine candidate derived from *V. cholerae* 01 El Tor Inaba (C6709) by deleting the cholera toxin CTX genetic element, introducing the gene encoding CT-B subunit into the rec A gene, and screening for non-motility. In a placebo-controlled clinical study, Peru-15 was orally administered to 11 North American volunteers at a dose of $2\times10^8$ cfu. No vaccinees developed diarrhea, and 10 shed vaccine organisms in stool. More than 200 Peru-15 stool isolates screened from all culture-positive volunteers showed no reversion to motility. Serologically, 10 vaccinees had >4-fold increases in serum vibriocidal antibody titers (the correlate of cholera immunity); peak geometric mean titer (GMT) of 1710; range 400–6400. This results are tabulated in Table 4.

One month after vaccination, 5 random vaccinees and 5 control volunteers were challenged with virulent *V. cholerae* 01 (N6961). Four of the 5 controls developed cholera with a mean diarrheal volume of 1.9 L. Two vaccinees developed diarrhea, 0.3 L and 1.0 L, respectively; the latter vaccinee had neither shed vaccine organisms nor responded serologically following Peru-15 vaccination. Challenge data suggest that significant serum vibriocidal responses positively predict vaccine efficacy. These results are tabulated in Table 5.

TABLE 4

Reactogenicity and Immunogenicity of Nonmotile El Tor 01 Inaba Vaccine Strain Peru-15

| | Vaccinees | Controls |
|---|---|---|
| No. with diarrhea | 0/11 | 0/3 |
| No. with severe symptoms[1] | 1/11 | 0/3 |
| No. positive for shedding[2] | 8/11 | 0/3 |

TABLE 4-continued

Reactogenicity and Immunogenicity of Nonmotile El Tor 01 Inaba Vaccine Strain Peru-15

| | Vaccinees | Controls |
|---|---|---|
| No. seroconv. for vibriocidal Ab | 10/11 | 0/3 |
| Peak geometric mean vibriocidal Ab titer | 1,710 | 0/3 |

[1]Defined as those symptoms interfering with normal activities or requiring treatment. Single positive vaccinee had a migraine headache and emesis at day 5.
[2]Average peak geometric mean titer for vaccinees was $2 \times 10^4$ per gram of stool.

TABLE 5

Challenge Study of Vaccinees Immunized with Nonmotile *V. cholerae* Strain Peru-15

| | Vaccinees | Controls |
|---|---|---|
| No. of volunteers with diarrhea | 2/5 | 4/5 |
| Diarrheal stool volume | 296/961[1] | 458-3,830 |
| No. with fever | >100.50/5 | 2/5 |
| No. with emesis | 0/5 | 2/5 |

[1]The vaccinee producing 961 ml of diarrheal stool was also the only vaccinee that did not seroconvert in vibiocidal titer after vaccination.

Chemistry, Manufacturing and Control of Peru-15

At the wild-type (and Peru-2) recA locus, the mixture of BglII and EcoRV, will generate two fragments: a-6.5 kb fragment derived from the EcoRV site downstream of the recA locus and an EcoRV or BglII site further downstream in chromosome sequence; and an −3.5 kb BglII/BglII fragment derived from a BglII site, upstream of, and a second BglII site, within, the recA locus. Both fragments will hybridize with the recA probe: neither fragment will hybridize with the CTX core probes. At the recA locus of successfully resolved merodiploids, these enzymes will generate a single, >8 kb, fragment derived from the BglII site upstream of the RecA locus and an EcoRV or BglII site further downstream in chromosome sequence. This fragment will hybridize with both the recA and CTX core probes.

Selection of a Motility Dysfunctional Isolate of Peru-3: Isolation of Peru-15

A vial of the Peru-3 seed lot was sampled and used to inoculate a 3 ml suspension culture in Luria broth containing 100 $\mu$g/ml streptomycin. Incubation at 30° C., without shaking, was continued for 16 to 18 hours. Approximately 2.9 ml of the culture medium was aspirated from the culture in a manner such as to leave the cell suspension at the bottom of the tub minimally disturbed. The residual cell suspension was removed from the tube and transferred into another culture tube containing 3 ml of Luria broth containing 100 $\mu$g/ml streptomycin. Incubation, aspiration, and reinoculation was repeated four additional times.

Following the fifth passage, cells from the bottom of the culture tube were diluted and plated onto Luria agar plates containing 100 $\mu$g/ml streptomycin. Sixty-eight single colonies were sampled from the agar surface with sterile toothpicks and stabbed into motility agar plates (0.4% agar, Luria broth. 100 $\mu$g/ml streptomycin). Dysfunctional motility was defined as reduced spreading from the site of inoculation, when compared to Peru-3, following overnight incubation at 30° C. 15 of sixty-eight isolates exhibited dysfunctional motility. Each of the 15 motility dysfunctional colonies were sampled from the motility plates and used to inoculate a 3 ml Luria broth. 100 $\mu$g/ml streptomycin, suspension culture, which was incubated overnight, at 30° C. with shaking.

A 100 μl aliquot of each overnight suspension was used to inoculate another 3 ml suspension culture which was incubated overnight, at 30° C. without shaking. Approximately 2.9 ml of the culture medium was aspirated from each of the 15 cultures in a manner such as to leave the cell suspension at the bottom of the tub minimally disturbed. Cells from the bottom of the 15 culture tubes ere streaked onto 15 Luria agar plates containing 100 μg/ml streptomycin, which were incubated overnight at 30° C. From each of the 15 Luria agar plates, 25 single colonies were sampled with sterile toothpicks and stabbed into individual motility agar plates (0.4% agar, Luria broth. 100 μg/ml streptomycin). On two of the plates all colonies exhibited dysfunctional motility; the colonies on these plates had been derived from two of the original 15 isolated, #2-29 and #2-35.

Clinical Testing of Bengal-15

Bengal-15 has been tested in human trials with favorable results relative to the control strain M010, as shown in Table 7. Only one of the four human recipients of the vaccine developed any diarrhea, and this was minor. All four subjects showed significant intestinal colonization. Table 8 provides a detailed listing of systemic symptoms following ingestion of Bengal-15 by volunteers. Tables 9, 10 and 11 show the favorable challenge results achieved when wild-type cholera was given to volunteers previously immunized with Bengal-15. Results with unvaccinated volunteers also challenged with wild-type cholera are provided as a control.

TABLE 6

Mouse Colonization Data on Motile and Nonmotile Vibrio cholerae Vaccine Strains[a]

| Strain | Motility | Serogroup/ Biotype/ Serotype | Average CFU/mouse |
|---|---|---|---|
| Bah-3 | Yes | 01/El Tor/Ogawa | $1.3 \times 10^6$ |
| Bah-15 | No | 01/El Tor/Ogawa | $5.2 \times 10^5$ |
| Bang-3 | Yes | 01/El Tor/Inaba | $1.2 \times 10^7$ |
| Bang-15 | No | 01/El Tor/Inaba | $7.0 \times 10^5$ |
| Bengal-3 | Yes | 0139/Bengal/ | $1.4 \times 10^7$ |
| Bengal-15 | No | 0139/Bengal/ | $6.3 \times 10^6$ |

[a]Strains were orally administered to 3–7 day old CD-1 mice. After 18 hours, mouse intestines were removed, homogenized, and plated for viable counts (colony forming units, CPU). Each strain was tested in 4–5 mice and the values reported are averages. Note also that in control experiments, non-colonizing strains (such as TcpA negative mutants) give average CFU/mouse values of less than $1 \times 10^2$.

TABLE 7

CLINICAL RESPONSE TO WILD TYPE (MO10) AND ATTENUATED 0139 Cholerae VACCINE PROTOTYPES

| Volunteer Letter Code | Age Race Sex | Symptoms | Diarrheal Stool Volume | Number of Diarrheal Stools | Culture (Date of Positive) | TCN Treatment |
|---|---|---|---|---|---|---|
| MO10 | | | | | | |
| A | 40/B/F | malaise gurgling | 276 | 2 | 12/2–3 | 12/1 |
| E | 30/B/M | malaise gurgling cramps | 1257 | 7 | 11/30–12/4 | 12/1 |
| F | 18/W/F | malaise gurgling cramps T 100.4 | 758 | 6 | 12/1–2 | 12/1 |
| VRI-16 | | | | | | |
| B | 35/B/F | None | 0 | 0 | Negative | 12/5 |
| G | 22/B/M | None | 0 | 0 | 12/2, 12/4 | 12/5 |
| K | 21/B/F | cramps | 0 | 0 | 12/2 | 12/5 |
| O | 37/B/F | None | 0 | 0 | 12/2 | 12/5 |
| BENGAL-3 | | | | | | |
| C | 36/B/M | gas | 0 | 0 | 12/3, 12/5 | 12/5 |
| I | 21/W/M | None | 0 | 0 | 12/2, 12/4 | 12/5 |
| L | 26/B/M | cramps | 312 | 1 | 12/1–4 | 12/2 |
| N | 38/B/M | malaise, cramps | 0 | 0 | 12/1 | 12/4 |
| BENGAL-15 | | | | | | |
| D | 28/B/M | cramps × 3 d | 0 | 0 | 12/1, 12/3 | 12/5 |
| H | 28/W/M | none | 0 | 0 | 12/4 | 12/5 |
| J | 24/W/M | malaise | 160* | 1 | 11/30–12/3 | 12/3 |
| M | 32/B/M | none | 0 | 0 | 12/1 | 12/5 |

* = not scored as diarrhea because volume less than 30 mls

TABLE 8

| Systemic Symptoms Following Ingestion of Nonmotile 0139 Vaccine Strain Bengal-15 | | |
|---|---|---|
| | Bengal-15 | Butter Control |
| Number of volunteers | 10 | 3 |
| % excreting vaccine | 90 | 0 |
| % with diarrhea | 0 | 0 |
| % with other symptoms | | |
| Headache | 50 | 33 |
| Muscle aches | 0 | 33 |
| Malaise | 30 | 66 |
| Abdominal gurgling | 40 | 33 |
| Abdominal cramps | 40 | 66 |
| Stomach gas | 70 | 100 |

TABLE 9

| Bengal-15 Immunological Response in Volunteers | | | | |
|---|---|---|---|---|
| | Vibriocidal antibody[1] | | | |
| | Day 0 | Day 14 | Day 28 | Peak anti-CT-B Titers[2] |
| Vaccinees | | | | |
| 1 | <5 | 640 | 160 | 15 |
| 2 | 20 | 80 | 10 | <5 |
| 3 | <5 | 640 | 640 | 15 |
| 4 | <5 | 80 | 40 | 15 |
| 5 | <5 | 640 | 80 | <5 |
| 6 | <5 | 640 | 160 | 15 |
| 7 | <5 | 320 | 160 | 15 |
| 8 | <5 | 160 | 40 | 15 |
| 9 | <5 | 160 | <5 | 45 |
| 10 | <5 | <5 | <5 | <5 |
| Controls | | | | |
| 1 | <5 | <5 | <5 | <5 |
| 2 | <5 | <5 | <5 | <5 |
| 3 | <5 | <5 | <5 | <5 |

[1]MO10T4 used as the target strain in the vibriocidal assay.
[2]Anti-CT-B titers are expressed as peak reciprocal values.

TABLE 10

| Bengal-15 Challenge Study[1] | | |
|---|---|---|
| Immunization status | Bengal-15 | Controls |
| Number of volunteers | 7 | 6 |
| Diarrhea attack rate | 1 (14%) | 5 (85%) |
| Mean no. diarrheal stools | 3 | 12 |
| Mean diarrheal output (L) | 0.4 | 3.7 |
| Incubation period (mean h) | 95 h | 26 h |
| Excretion of challenge strain | 3 (42%) | |
| Vaccine efficacy | 83% | |
| Fishers exact test 1-tail | P = 0.025 | |

[1]Challenge was a single 5 × $10^6$ dose of *V. cholerae* 0139 strain MO10

TABLE 11

| Challenge Study[1] Bengal-15 of Vaccinees and Control Subjects | | | |
|---|---|---|---|
| Vaccinees | Diarrheal stool output volume (ml) | No. of Diarrheal stools | Incubation period (hrs) |
| 1 | 0 | | — |
| 2 | 0 | — | — |
| 3 | 394 | | 395 |
| 4 | 85 | | 122 |
| 5 | 0 | — | — |
| 6 | 0 | — | — |
| 7 | 0 | — | — |
| Controls | | | |
| 1 | 4876 | | 1021 |
| 2 | 0 | 0 | 0 |
| 3 | 7800 | 22 | 45 |
| 4 | 1374 | 6 | 21 |
| 5 | 3015 | 13 | 22 |
| 6 | 1667 | 7 | 20 |

[1]*V. cholerae* 0139 strain MO10 was given at a dose of 5 × $10^6$ cfu.

Example 4

Isolation of soft agar penetration-defective strains by transposon mutagenesis.

A. Identification and sequencing of motB in *V. cholerae*

Transposon insertions in *V. cholerae* strain 0395($Lac^-$) were generated using the protocol provided above and depicted in FIG. 2. Virtually any *V. cholerae* strain may, however, be used in with the Tnlac transposon used this protocol so long as it is $Lac^-$. Using this protocol, $Mot^-$ $Fla^+$ and $Mot^-Fla^-$ soft agar penetration-defective strains were obtained. We then sequenced the insertion joints from one of the $Mot^-Fla^+$ mutants.

DNA from Tnlac is sequenced using the following protocol. Chromosomal DNA was made from the Tnlac insertion strains using standard protocols. 1–2 μg of DNA was then cut overnight with an enzyme chosen from the following group: PstI, TagI, SachI, Xhol, Aval, Mscl, BanL, Ddel, TthIII (those in bold are most preferable). DNA was Phenol extracted with 2× phenol and 2× chloroform, then ethanol precipitated. Dried digested sample were resuspended in 10 μl and 0.5 μg of digested DNA was then put in sterile Eppindorf tubes (1.5 ml) with 150 μl sterile water, 50 μl 10 ×T4 DNA ligation buffer (with neither BSA nor spermidine) and 500 units of T4 DNA Ligase were added. The test tube was then incubated 12–16 hrs. at 14° C. 50 μl (1/10) of the mixture was used to do PCR. Ligated DNA was de-salted in spin columns followed by ethanol precipitation prior to PCR.

PRC conditions are as follows. 30 cycles were done at 95° C. for 1', 50° C for 2' and 73° C. 2.' The following primers may be used to sequence all Tnlac insertion junctions:

5' CCATCTCATCAGAGGGTAGT 3' (SEQ ID No.1) (this oligonucleotide reads into the transposon)

5' ACCATGTTAGGAGGTCACAT 3' (SEQ ID No. 2) (this oligonucleotide reads out the right end of the transposon).

Products of the PCR reaction were put over a column to remove primers and sequencing was done directly, although bands may be gel purified using low melting agarase run on a high % gel followed by cutting out on the band in a small volume and heating at 65° C. for 10'. When bands are cut out using the later method 1 unit of agarase is used for every 100 μl of gel, and the agarase mixture is then incubated for 1 hour at 37° C., and then sequencing is done directly.

B. Construction of deletions for use in *V. cholerae* vaccines.

Once the sequence of the gene of interest has been determined and the loss of function phenotype has been determined to be desirable for vaccine use, full length clones may be obtained from *V. cholerae* libraries and disruptions (deletions or insertions which have a low reversion frequency) may be constructed using standard protocols in molecular biology and as described herein. These deletions may then be recombined into the chromosome using the techniques provided, for example, in Mekalanos' U.S. Ser. No. 08/083,388, filed Jun. 28, 1993.

The insertion points of one soft agar penetration-defective transposon insertion were sequenced to demonstrate the identification of these putative motility and chemotaxis genes. The gene was determined to be the *V. cholerae* homolog of *E. coli* motB (see Table 2 and FIG. 4, SEQ ID No. 3). The accuracy of this determination is supported by the finding that this insertion mutation confers a $Mot^-$ $Fla^+$ phenotype, as would be expected for a motB insertion in *E. coli*

Example 5

Isolation of soft agar penetration-defective mutants by homology cloning and disruption: cloning of fliC.

The method used to isolate the *V. cholerae* fliC homologue is provided in Mekalanos and Camilli, U.S. patent application filed on Sep. 28, 1993, hereby incorporated by reference). Briefly, the method is as follows: a plasmid vector pIVET5 was constructed which allows one to screen for bacterial genes which are induced in host tissues. Random partially digested Sau3AI DNA fragments of the *V. cholerae* chromosome were cloned into a single BamHI restriction site in pIVET5 immediately 5' to a promoterless synthetic operon consisting of a site-specific DNA recombinase and the *E. coli* lacZY reporter coding sequences. The recombinant plasmid library was moved into a *V. cholerae* reporter strain that contains a lacZ::res1-tet-res1 allele on the chromosome (*V. cholerae* lacZ gene not *E. coli*. The plasmids behave as suicide vectors in *V. cholerae* and must therefore integrate into the chromosome by homologous recombination. Transcriptional fusions of *V. cholerae* chromosomal genes to the promoterless synthetic operon on the integrated plasmid can result, upon induction of the chromosomal gene promoter, in expression of the site specific recombinase and lacZY reporter genes. The recombinase specifically catalyzes recombination at the resi sequences flanking the tet gene, resulting in excision of the tet gene and subsequent loss of tetracycline resistance in descendent bacteria. To screen for *V. cholerae* genes which are induced in the suckling-mouse model of cholerae, we screened for and pooled tetracycline resistant, $Lac^-$ colonies in vitro on L-agar plates supplemented with tetracycline and XG. These represent bacteria having no or transcriptionally inactive gene fusions to the promoterless synthetic operon on the integrated plasmids. These colonies were pooled together and used to orally infected suckling mice. After 24 hours bacteria were recovered form the small intestines and plated on L-agar. Resultant colonies were replica-plated to L-agar supplemented with tetracycline to screen for colonies which were tetracycline sensitive. These represent bacterial clones having a chromosomal gene or operon fused to the synthetic operon on the integrated plasmid which was induced at some time during infection of the mice. The integrated plasmid was cloned from one such strain. The fusion junction was sequenced using an outward reading oligonucleotide primer complementary to the 5' end of the site-specific recombinase gene and standard techniques.

One such clone, designated AC-V45-2 had a transcriptional fusion of the synthetic operon on the integrated plasmid to a gene on the *V. cholerae* chromosome divergently transcribed from the *V. cholerae* fliC homologue (see homology figure below). FliC is the major protein, flagellin, which comprises the flagella in many bacterial species. The identity of the gene or operon fused to the synthetic operon is unknown at this time. However, it presumably is involved in motility as is the case for S. typhimurium where immediately upstream and divergently transcribed from fliC is the fliDST operon encoding a putative flagella cap protein and two regulatory genes, respectively (Macnab review). Thus, our method has indirectly identified the fliC homologue of *V. cholerae* by directly identifying physically linked gene(s) that may be involved in motility. This method may allow identification of other gene(s) involved in motility of *V. cholerae.*

Deletion of the *V. cholerae* fliC gene to generate an aflagellate mutant strain can be easily accomplished as follows. The entire fliC gene can be cloned from AC-V45-2 by digesting chromosomal DNA with an infrequent-cutting restriction enzyme such as SaII which has a site downstream of the synthetic operon on the integrated plasmid, but which does not have sites within the synthetic operon nor within the sequenced portion of fliC. This DNA fragment will contain most if not all of fliC as well as the synthetic operon. The entire chromosomal SaII digested DNA will be cloned into the SaII site of pBR322 (Watson, N. (1988) *Gene* 70:399–403) by ligation, electroporated into *E. coli*, DH5$\alpha$, and $LacZ^+$ bacteria screened for on L-agar supplemented with ampicillin and X-gal. Such $LacZ^+$ clones will contain the sought-after recombinant plasmid containing fliC and the synthetic operon. The fliC gene will be restriction enzyme mapped using standard techniques. A non-revertible mutation in fliC consisting of a deletion of a large internal fliC DNA fragment will be made using the appropriate restriction enzymes followed by self-ligation. The ΔfliC allele on the resulting plasmid will be used to replace the wild-type fliC gene on the bacterial chromosome by allele exchange using the previously described and commonly used technique of double crossover via homologous recombination (Hamilton, C. (1989) *J. Bacteriol.* 171:4617–4622). The ΔfliC mutation in the resulting *V. cholerae* strain will be confirmed by southern blot analysis using a fliC-containing DNA plasmid probe. Such a strain will be non-motile and aflaggellate because the flagellin protein will not be made due to deletion of fliC. This technique of allelic exchange can be used to generate non-reverting deletion mutations in any of the motility genes of *V. cholerae.*

Example 6

Bivalent Vaccine Results

The most straightforward approach for testing a bivalent vaccine is to make determination of whether both vaccine candidates can co-colonize the mouse and rabbit intestine. The infant mouse colonization model has proven valuable in predicting the level of *V. cholerae* colonization in the human intesting Pearson et al., PNAS USA, 90:3750–3754, (1993)), and the adult rabbit immunogenicity model has proven valuable in predicting the immunogenicity of *V. cholerae* in humans, (Albert et al., Proceeding of the 29th Joint Conference, U.S.—Japan Cooperative Medical Science Program and Related Diarrheal Diseases. Monterey, Calif. (1993)). The aim of the present experiment was to determine whether 01 vaccine candidates can colonize the mouse and rabbit intestine compatibly with 0139 vaccine candidate Bengal-15 and, most importantly, provoke 01- and 0139-specific immune responses in the rabbit. We have found that both co-colonization and immunogenicity can be achieved with a bivalent vaccine.

Infant mouse colonization study:

Administration protocol: three to five day old sucking CD-1 mice housed 5 mice per group were inoculated orally with 50 $\mu$l of *V. cholerae* in Luria broth using PE-10 tubing on the end of a 1 cc syringe. After 24 hours, the mice were sacrificed by $CO_2$ narcosis, and the small intestines were harvested. Intestines were homogenized, diluted and plated on Luria agar containing 100 $\mu$l streptomycin sulfate. The results follow.

| | Input cfu | Output cfu |
|---|---|---|
| Peru-14 | $3.4 \times 10^5$ | $4.8 \times 10^5$ |
| Bengal-15 | $6.9 \times 10^4$ | $7.4 \times 10^3$ |

Five mice per group

Adult rabbit immunogenicity study:

Immunization protocol: 9–11 week old, 1.5–2 kg, male SPF New Zealand white rabbits from either Hazelton Research Products or Charles River Laboratories are housed individually in stainless steel caging allowing 4 square feet per rabbit. Rabbits are fasted overnight. Rabbits are then anesthetized with 30 mg/kg Ketamine and 3 mg/kg Zylazine plus Acepromazine intramuscularly (IM). If needed, an additional 15 mg/kg Ketamine is delivered IM to maintain sedation. A prebleed is drawn from the auricular artery. A rectal swab using a sterile cotton tipped applicator is taken and plated on TCBS agar. At time 0, 50 mg/kg cimetidine is delivered IV to the marginal ear vein. At time=15 minutes 10 ml $NaHCO_3$ is delivered by orogastric feeding tube attached to a 30 cc syringe. At time=30 minutes another 10 ml $NaHCO_3$ is delivered orally, followed by immediately by the dose of *V. cholera* in 10 ml LB media delivered orally. At time=60 minutes, 1 ml of tincture of opium containing 10 mg morphine is delivered intraperitoneally (IP). The rabbits are then returned to their cages are allowed to eat and drink. Rectal swabs are taken on days 1, 3, 5, 7, 14, 21, and 28. Weekly bleeds to recover sera are done on days 7, 14, 21, and 28 following inoculation. On day 28, animals are sacrificed by first sedating by IM injection of ketamine/xylazine (44 mg/kg ketamine, 2.5 mg/kg xylazine) followed by lateral ear vein injection of the lethal dose of sodium pentobarbital 1 ml/10 lbs. The results are shown in Table 12.

V. DEPOSITS

Under the terms of the Budapest Treaty on the International Recognition of the Deposit of Microorganisms for the Purpose of Patent Procedure, deposit of *V. cholerae* strains C6709-Sm, P27459-Sm, E7946-Sm, Bengal-2, Bengal-3, MO10, VRI-16, Bengal-15, Peru-14, Peru-15, Bah-15, and Bang-15 have been made with the American Type Culture Collection (ATCC) of 10801 University Blvd., Manassas, Va., 20110-2209, USA, where the deposits were given ATCC Accession Numbers ATCC 55331 (C6709-Sm) deposited Jun. 24, 1992; ATCC 55333 (P27459-Sm) deposited June 24, 1992; ATCC 55332 (E7946-Sm) deposited Jun. 24, 1992; ATCC 55436 (0139, Bengal-2) deposited Jun. 14, 1993; ATCC 55437 (0139, Bengal-3) deposited Jun. 14, 1993; ATCC 55438 (0139, MO10) deposited Jun. 14, 1993; ATCC 55463 (Bengal-15) deposited Aug. 10, 1993; ATCC 55446 (Peru-14) deposited Jun. 30, 1993; ATCC 55866 (Peru-15) deposited Dec. 2, 1994; ATCC 55634 (Bah-15) Dec. 2, 1994; deposited ATCC 55636 (Bang-15) deposited Dec. 2, 1994.

Applicants' assignees, President and Fellows of Harvard College and Virus Research Institute, Inc., represent that the ATCC is a depository affording permanence of the deposit and ready accessibility thereto by the public if a patent is granted. All restrictions on the availability to the public of the material so deposited will be irrevocably removed upon granting of a patent. The material will be available during the pendency of the patent application to one determined by the Commissioner to be entitled thereto under 37 C.F.R. 1.14 and 35 U.S.C. § 122. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicants' assignees acknowledge their duty to replace the deposit should the depository be unable to furnish a sample when requested due to the condition of the deposit.

Further embodiments of the invention are within the following claims:

TABLE 12

SUMMARY OF RABBIT IMMUNE RESPONSE DATA FROM PERU AND BENGAL ORAL IMMUNIZATIONS

| | VIBRIOCIDAL (O1) | | | | VIBRIOCIDAL (O139) | | | | CtxB ELISA | | | |
|---|---|---|---|---|---|---|---|---|---|---|---|---|
| | 0 | 13 | 21 | 28 | 0 | 13 | 21 | 28 | 0 | 14 | 21 | 28 |
| Peru-14/Bengal-15 ($2 \times 10^9$) ($8 \times 10^9$) | <25 | 1600 | 1600 | 1600 | <25 | 100 | 200 | 400 | <10 | <10 | 80 | 160 |
| Peru-14/Bengal-15 ($7 \times 10^8$) ($1 \times 10^{10}$) | <25 | 200 | 200 | 200 | <25 | 200 | 200 | 200 | <10 | <10 | 80 | 160 |
| Peru-14/Bengal-15 ($4 \times 10^9$) ($1 \times 10^9$) | <25 | 400 | 400 | 400 | <25 | 100 | 100 | 100 | <10 | <10 | <10 | <10 |
| Peru-15 ($9 \times 10^9$) | <25 | 3200 | 3200 | 3200 | <25 | <25 | <25 | <25 | <10 | <10 | <10 | <10 |
| Peru-15/Bengal-15 ($4 \times 10^9$) ($6 \times 10^9$) | <25 | 800 | 1600 | 3200 | <25 | 100 | 100 | 100 | <10 | <10 | 160 | 160 |
| Peru-15/Bengal-15 ($5 \times 10^9$) ($3 \times 10^9$) | <25 | 200 | nd | nd | <25 | <25 | nd | nd | nd | nd | nd | nd |
| Peru-15/Bengal-15 ($1 \times 10^9$) ($6 \times 10^9$) | <25 | 25 | nd | nd | <25 | 200 | nd | nd | nd | nd | nd | nd |
| Peru-15/Bengal-15 ($6 \times 10^9$) ($1 \times 10^9$) | <25 | 400 | nd | nd | <25 | 200 | nd | nd | nd | nd | nd | nd |

What is claimed is:

1. A genetically stable vaccine comprising a nontoxinogenic genetically stable mutant strain of *Vibrio cholerae*, said mutant strain being a mutan: of a parental strain, said mutant strain comprising a deletion ot DNA encoding the CtxA subunit such that said strain lacks a subunit A of cholera toxin, and said mutant strain further exhibiting a soft agar penetration-defective phenotype relative to said parental strain wherein said vaccine is in a physiologically acceptable carrier.

2. The vaccine of claim 1, wherein said mutant strain is further lacking any functional attRS1 sequences.

3. The vaccine of claim 1, wherein said mutant strain is derived from a parental strain belonging to the El Tor biotype.

4. The vaccine of claim 3, wherein said parental mutant strain is of the Inaba or Ogawa serotype.

5. The vaccine of claim 4, wherein said parental strain is Peru-2 (ATCC 55865).

6. The vaccine of claim 4, wherein said parental strain is Peru-3 (ATCC 55866).

7. The vaccine of claim 4, wherein said parental strain is Bah-2 (ATCC 55859).

8. The vaccine of claim 4, wherein said parental strain is Bah-3 (ATCC 55860).

9. The vaccine of claim 4, wherein said parental strain is Bang-2 (ATCC 55862).

10. The vaccine of claim 4, wherein said parental strain is Bang-3 (ATCC 55863).

11. The vaccine of claim 1, wherein said mutant strain lacks CTX core sequences.

12. The vaccine of claim 1, wherein said mutant strain further lacks a functional recA gene.

13. The vaccine of claim 12, wherein said strain is $ctx^-$.

14. The vaccine of claim 1, wherein said strain further encodes a B subunit of *Vibrio cholerae* toxin.

15. A vaccine comprising at least two different strains of *Vibrio cholerae* according to claim 1.

16. A genetically stable vaccine comprising a nontoxinogenic genetically stable mutant strain of *Vibrio cholerae*, said mutant strain being a mutant of a parental strain, said mutant strain comprising a deletion of DNA encodine the CtxA subunit such that said strain lacks a reactogenic subunit A of cholera toxin, wherein at least 25% of the cells of said strain are capable of forming filamentous structures of 15 nM or greater under conditions of stationary phase growth wherein said vaccine is in a physiologically acceptable carrier.

17. The vaccine of claim 1, wherein said mutant strain is $Mot^-$.

18. The Mot vaccine of claim 17, wherein said $Mot^-$ phenotype is resulting from a disruption of the motB gene.

19. The vaccine of claim 1, wherein said mutant stain is $Fla^-$.

20. The $Fla^-$ vaccine of claim 19, wherein said $Fla^-$ phenotype is resulting from a disruption in the fliC gene.

21. The vaccine of claim 1, wherein said strain has a 5-fold or greater decrease in HEp-2 binding relative to said parent strain.

22. A method of vaccinating against cholerae by administering the vaccine of claim 1.

23. A method of making a killed *Vibrio cholerae* vaccine, said method comprising the steps of providing at least one mutant strain exhibiting a soft agar penetration-defective phenotype, which strain has been killed;

adding to said killed strain cholerae toxin B subunit produced by said strain wherein said toxin B subunit is obtained from the medium in which said strain was propagated; and suspending said killed strains and said toxin B subunit in a physiologically acceptable carrier.

24. The vaccine of claim 17, wherein said $Mot^-$ phenotype is resulting from a genetically engineered disruption of a motility gene.

25. The vaccine of claim 20, wherein said $Fla^-$ phenotype is resulting from a genetically engineered disruption of a flagellar gene.

26. The vaccine of claim 1, wherein said mutant strain further comprises a deletion of attRS1 sequences.

* * * * *

UNITED STATES PATENT AND TRADEMARK OFFICE

CERTIFICATE OF CORRECTION

PATENT NO. : 6,203,799 B1 
DATED : March 20, 2001
INVENTOR(S) : John J. Mekalanos et al.

It is certified that error appears in the above-identified patent and that said Letters Patent is hereby corrected as shown below:

Title page,
Item [73], Assignee, replace "Presidents" with -- President --;
Item [56], OTHER PUBLICATIONS, replace "Taylor et al," with -- Taylor et al., --;
Kaper et al., replace "Wachsmuth et al pp." with -- Wachsmuth et al., pp. --;
Tacket et al., replace "Tacket et al Infect." with-- Tacket et al., Infect. --;
Ichinese et al., replace "Ichinese et al, Infect" with -- Ichinese et al., Infect. --;
Trucksis et al., replace "Trucksis et al," with-- Trucksis et al., --;

Column 2,
Line 22, replace "at 300." with -- at 30º. --;
Line 57, replace "flit" with -- fliT --;
Line 58, replace "flIF" with -- fliF --;
Line 59, replace "flgj" with -- flgJ --, and replace "flil" with -- fliL --;

Column 8,
Lines 1, 4 and 8, replace "300" with -- 30º --;
Lines 64-65, replace *"is so closely related (see Examples" with*
-- is so closely related (see Examples --;

Column 9,
Line 28, replace "HED-2" with -- HEp-2 --;

Column 10,
Line 45, begin a new paragraph after "Use of the Live Vaccine Strains.";

Column 11,
Line 65, replace "theabsence" with -- the absence --;

Column 18,
Line 35, replace "SachI" with -- SacII --, and replace "PstI, TagI, SacII, Xhol," with
-- PstI, TagI, SacII, Xhol, --;

Column 19,
Line 41, replace "resi" with -- res1 --;

UNITED STATES PATENT AND TRADEMARK OFFICE

CERTIFICATE OF CORRECTION

PATENT NO. : 6,203,799 B1 
DATED : March 20, 2001
INVENTOR(S) : John J. Mekalanos et al.

It is certified that error appears in the above-identified patent and that said Letters Patent is hereby corrected as shown below:

Column 27,
Line 30, replace “mutan:” with -- mutant --;
Line 31, replace “ot” with -- of --;

Column 28,
Line 36, replace “Mot vaccine” with -- Mot$^{-}$ vaccine --.

Signed and Sealed this

Twenty-seventh Day of August, 2002

*Attest:*

JAMES E. ROGAN

*Attesting Officer* *Director of the United States Patent and Trademark Office*